US012703098B2

(12) United States Patent
Ruffaldi et al.

(10) Patent No.: US 12,703,098 B2
(45) Date of Patent: Aug. 11, 2026

(54) METHOD FOR VERIFYING THE INTEGRITY OF A MASTER DEVICE OF A MASTER-SLAVE ROBOTIC SYSTEM FOR MEDICAL OR SURGICAL TELEOPERATION AND RELATED ROBOTIC SYSTEM

(71) Applicant: MEDICAL MICROINSTRUMENTS, INC., Wilmington, DE (US)

(72) Inventors: Emanuele Ruffaldi, Pisa (IT); Massimiliano Simi, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 0 days.

(21) Appl. No.: 18/546,171

(22) PCT Filed: Feb. 14, 2022

(86) PCT No.: PCT/IB2022/051286
§ 371 (c)(1),
(2) Date: Aug. 11, 2023

(87) PCT Pub. No.: WO2022/175800
PCT Pub. Date: Aug. 25, 2022

(65) Prior Publication Data

US 2024/0131713 A1 Apr. 25, 2024
US 2024/0227191 A9 Jul. 11, 2024

(30) Foreign Application Priority Data

Feb. 16, 2021 (IT) ........................ 102021000003488

(51) Int. Cl.
*B25J 9/16* (2006.01)
*A61B 34/20* (2016.01)
*A61B 34/35* (2016.01)

(52) U.S. Cl.
CPC ............. *B25J 9/1689* (2013.01); *A61B 34/20* (2016.02); *A61B 34/35* (2016.02); *B25J 9/1674* (2013.01);
(Continued)

(58) Field of Classification Search
CPC ........ B25J 9/1689; B25J 9/1674; B25J 13/02; B25J 19/0095; B25J 19/02; B25J 9/0009;
(Continued)

(56) References Cited

U.S. PATENT DOCUMENTS 5,943,914 A 8/1999 Morimoto
6,063,095 A 5/2000 Wang
(Continued)

FOREIGN PATENT DOCUMENTS

CN 107690302 A 2/2018
CN 109196429 A 1/2019
(Continued)

OTHER PUBLICATIONS

International Search Report and Written Opinion received for PCT Serial No. PCT/IB2022/051226 on Apr. 8, 2022, 15 pgs.
(Continued)

*Primary Examiner* — Esvinder Singh
(74) *Attorney, Agent, or Firm* — Merchant & Gould P.C.

(57) ABSTRACT

A method verifies functional/structural integrity of a hand-held unconstrained master device to control a robotic system for medical or surgical teleoperation. The master device includes a body having two rigid parts constrained to relatively rotate or translate on a common axis. Position vectors of two-plus points are measured and/or detected, each belonging to a respective one of the two rigid parts, and measuring and/or detecting evolution of the position vectors. An orientation of each of the points, and the evolution of the orientations are measured and/or detected. Constraints from
(Continued)

constructional/structural features of the master device are defined, deriving from degrees of freedom. Mathematical relations associated with each of the defined constraints are calculated based on detected and/or measured position vectors, orientations and evolutions. A state of functional/structural integrity or non-integrity of the master device is determined, based on verification of the mathematical relations and degrees of freedom.

20 Claims, 11 Drawing Sheets

(52) U.S. Cl.
CPC ................ *A61B 2034/2051* (2016.02); *A61B 2034/2055* (2016.02)

(58) Field of Classification Search
CPC .......... B25J 9/1602; B25J 9/1653; B25J 3/00; A61B 34/20; A61B 34/35; A61B 2034/2051; A61B 2034/2055; A61B 90/06; A61B 2034/2046; A61B 2034/2059; A61B 2090/067; A61B 34/25; A61B 34/37; A61B 34/74; A61B 2017/00725; A61B 34/30; G05B 2219/39413; G05B 2219/1215; G05B 2219/2231; G05B 2219/39122; G05B 2219/39139; G05B 2219/39141; G05B 2219/39145; G05B 2219/40401; G05B 2219/40405
See application file for complete search history.

(56) References Cited

U.S. PATENT DOCUMENTS 6,364,888 B1 4/2002 Niemeyer
6,424,885 B1 7/2002 Niemeyer
6,459,926 B1 10/2002 Nowlin
6,594,552 B1 7/2003 Nowlin
6,671,581 B2 12/2003 Niemeyer
6,766,204 B2 7/2004 Niemeyer
6,879,880 B2 4/2005 Nowlin
7,087,049 B2 8/2006 Nowlin
7,155,315 B2 12/2006 Niemeyer
7,331,967 B2 2/2008 Lee
7,373,219 B2 5/2008 Nowlin
7,778,733 B2 8/2010 Nowlin
7,806,891 B2 10/2010 Nowlin
7,886,743 B2 2/2011 Cooper
7,947,050 B2 5/2011 Lee
7,967,137 B2 6/2011 Fulbrook
8,004,229 B2 8/2011 Nowlin
8,005,571 B2 8/2011 Sutherland
8,123,740 B2 2/2012 Madhani
8,220,468 B2 7/2012 Cooper
8,281,670 B2 10/2012 Larkin
8,368,649 B2 2/2013 Hall
8,375,808 B2 2/2013 Blumenkranz
8,521,331 B2 8/2013 Itkowitz
8,540,748 B2 9/2013 Murphy
8,543,240 B2 9/2013 Itkowitz
8,620,473 B2 12/2013 Diolaiti
8,638,057 B2 1/2014 Goldberg
8,677,820 B2 3/2014 Nakagawa
8,812,160 B2 8/2014 Hagn
8,831,782 B2 9/2014 Itkowitz
8,935,003 B2 1/2015 Itkowitz
8,939,963 B2 1/2015 Rogers
8,996,173 B2 3/2015 Itkowitz
9,060,796 B2 6/2015 Seo
9,101,379 B2 8/2015 Au
9,333,042 B2 5/2016 Diolaiti
9,387,043 B2 7/2016 Yang
9,408,668 B2 8/2016 Durant
9,452,020 B2 9/2016 Griffiths
9,492,927 B2 11/2016 Diolaiti
9,554,866 B2 1/2017 Cunningham
9,629,680 B2 4/2017 Winer
9,632,573 B2 4/2017 Ogawa
9,707,684 B2 7/2017 Ruiz Morales
9,743,989 B2 8/2017 Itkowitz
9,770,300 B2 9/2017 Kwon
9,855,662 B2 1/2018 Ruiz Morales
9,901,402 B2 2/2018 Itkowitz
9,949,799 B2 4/2018 Hingwe
9,968,405 B2 5/2018 Cooper
10,013,082 B2 7/2018 Schecter
10,034,718 B2 7/2018 Griffiths
10,052,164 B2 8/2018 Overmyer
10,085,810 B2 10/2018 Vakharia
10,123,844 B2 11/2018 Nowlin
10,188,472 B2 1/2019 Diolaiti
10,219,870 B2 3/2019 Mondry
10,219,898 B2 3/2019 Forsell
10,271,915 B2 4/2019 Diolaiti
10,292,661 B1 5/2019 LaBorde
10,299,873 B2 5/2019 Hares
10,299,883 B2 5/2019 Kilroy
10,307,199 B2 6/2019 Farritor
10,321,964 B2 6/2019 Grover
10,357,320 B2 7/2019 Beira
10,357,324 B2 7/2019 Flatt
10,376,323 B2 8/2019 Farritor
10,376,337 B2 8/2019 Kilroy
10,383,699 B2 8/2019 Kilroy
10,393,109 B2 8/2019 Wu
10,413,374 B2 9/2019 Chassot
10,420,618 B2 9/2019 Grover
10,470,830 B2 11/2019 Hill
10,485,621 B2 11/2019 Morrissette
10,512,514 B2 12/2019 Nowlin
10,512,515 B2 12/2019 Bailey
10,524,871 B2 1/2020 Liao
10,531,929 B2 1/2020 Widenhouse
10,543,050 B2 1/2020 Itkowitz
10,561,468 B2 2/2020 Cunningham
10,568,703 B2 2/2020 Nobles
10,568,704 B2 2/2020 Savall
10,603,123 B2 3/2020 Vakharia
10,617,484 B2 4/2020 Kilroy
10,624,708 B2 4/2020 Hunter
10,639,114 B2 5/2020 Schuh
10,653,489 B2 5/2020 Kopp
10,661,453 B2 5/2020 Koenig
10,736,701 B2 8/2020 Savall
10,736,706 B2 8/2020 Scheib
10,751,136 B2 8/2020 Farritor
10,758,298 B2 9/2020 Felder
10,779,898 B2 9/2020 Hill
10,786,327 B2 9/2020 Anderson
10,789,329 B2 9/2020 Lanting
10,813,713 B2 10/2020 Koch
10,820,953 B2 11/2020 Kralicky
10,842,577 B2 11/2020 Kilroy
10,842,581 B2 11/2020 Bailey
10,881,477 B1 1/2021 Genova
10,888,390 B2 1/2021 Higuchi
10,898,281 B2 1/2021 Cooper
10,912,618 B2 2/2021 Vakharia
10,959,798 B2 3/2021 Diolaiti
10,987,192 B2 4/2021 Garcia Kilroy
11,037,464 B2 6/2021 Ho
11,045,268 B2 6/2021 Grover
11,083,532 B2 8/2021 Liao
11,083,534 B2 8/2021 Hares
11,096,746 B2 8/2021 Savall
11,109,925 B2 9/2021 Cooper
11,135,031 B2 10/2021 Savall
11,172,997 B2 11/2021 Kostrzewski
11,179,209 B2 11/2021 Kralicky
11,179,211 B2 11/2021 Zemlok

(56) References Cited

U.S. PATENT DOCUMENTS 11,179,213 B2 11/2021 Huang
11,213,364 B2 1/2022 Popovic
11,246,670 B2 2/2022 Swayze
11,266,469 B2 3/2022 Fuerst
11,284,957 B2 3/2022 Denlinger
11,284,959 B2 3/2022 Bailey
11,344,374 B2 5/2022 Tekiela
11,357,597 B2 6/2022 Jhaveri
11,399,908 B2 8/2022 Diolaiti
11,406,465 B2 8/2022 Zemlok
11,439,478 B2 9/2022 Anderson
11,446,097 B2 9/2022 Savall
11,457,987 B2 10/2022 He
11,478,318 B2 10/2022 Cone
11,478,928 B2 10/2022 Hariri
11,484,379 B2 11/2022 Sutherland
11,504,197 B1 11/2022 Noonan
11,504,203 B2 11/2022 Flatt
11,534,246 B2 12/2022 Fuerst
11,534,252 B2 12/2022 DiMaio
11,576,733 B2 2/2023 Anglese
11,607,279 B2 3/2023 Chaplin
11,666,401 B2 6/2023 Denlinger
11,684,434 B2 6/2023 Shelton
11,707,336 B2 7/2023 Itkowitz
11,712,314 B2 8/2023 Thompson
12,048,505 B2 7/2024 Thompson
2002/0055795 A1 5/2002 Niemeyer
2002/0128552 A1 9/2002 Nowlin et al.
2003/0004610 A1 1/2003 Niemeyer
2003/0195664 A1 10/2003 Nowlin
2004/0039485 A1 2/2004 Niemeyer
2005/0194507 A1 9/2005 White
2006/0030840 A1 2/2006 Nowlin
2006/0106493 A1 5/2006 Niemeyer
2006/0241414 A1 10/2006 Nowlin
2007/0013336 A1 1/2007 Nowlin
2008/0114494 A1 5/2008 Nixon
2008/0154246 A1 6/2008 Nowlin
2009/0301927 A1 12/2009 Fulbrook
2010/0053085 A1 3/2010 Hall
2010/0094312 A1 4/2010 Ruiz Morales
2010/0274087 A1 10/2010 Diolaiti
2011/0118748 A1 5/2011 Itkowitz
2012/0011932 A1 1/2012 Nakagawa
2012/0059391 A1 3/2012 Diolaiti
2012/0071891 A1 3/2012 Itkowitz
2012/0071892 A1 3/2012 Itkowitz
2012/0316681 A1 12/2012 Hagn
2013/0012930 A1 1/2013 Ruiz Morales
2013/0035697 A1 2/2013 Ogawa
2013/0316681 A1 11/2013 Huang
2013/0321262 A1 12/2013 Schecter
2014/0018960 A1 1/2014 Itkowitz
2014/0160015 A1* 6/2014 Ogawa .................. A61B 34/76 345/156
2014/0171964 A1 6/2014 Yang
2014/0222021 A1 8/2014 Diolaiti
2015/0025549 A1 1/2015 Kilroy
2015/0038981 A1 2/2015 Kilroy
2015/0038982 A1 2/2015 Kilroy
2015/0066051 A1 3/2015 Kwon
2015/0080909 A1 3/2015 Itkowitz
2015/0157410 A1 6/2015 Kilroy
2015/0182289 A1 7/2015 Itkowitz
2016/0242860 A1 8/2016 Diolaiti
2016/0287279 A1 10/2016 Bovay
2017/0035521 A1 2/2017 Diolaiti
2017/0086931 A1 3/2017 Auld
2017/0095295 A1 4/2017 Overmyer
2017/0095298 A1 4/2017 Vakharia
2017/0156806 A1 6/2017 Prisco
2017/0224428 A1 8/2017 Kopp
2017/0252112 A1 9/2017 Crawford
2017/0265949 A1 9/2017 Crawford
2017/0312043 A1 11/2017 Ogawa
2017/0319284 A1 11/2017 Itkowitz
2018/0025666 A1 1/2018 Ho
2018/0036088 A1 2/2018 Kilroy
2018/0078034 A1 3/2018 Savall
2018/0078319 A1 3/2018 Nobles
2018/0078321 A1* 3/2018 Liao ...................... B25J 9/1689
2018/0092706 A1 4/2018 Anderson
2018/0161108 A1 6/2018 Savall
2018/0168681 A1 6/2018 Kirk
2018/0168759 A1 6/2018 Kilroy
2018/0194013 A1 7/2018 Ruiz Morales
2018/0214223 A1 8/2018 Turner
2018/0235719 A1 8/2018 Jarc
2019/0012006 A1 1/2019 Schecter
2019/0029770 A1 1/2019 Bailey
2019/0069960 A1 3/2019 Vakharia
2019/0110847 A1 4/2019 Diolaiti
2019/0142530 A1 5/2019 Thompson
2019/0201152 A1 7/2019 Diolaiti
2019/0239972 A1* 8/2019 Chassot ............ A61B 18/1442
2019/0307524 A1 10/2019 Popovic
2019/0314097 A1 10/2019 Diolaiti
2019/0343594 A1 11/2019 Garcia Kilroy
2019/0380791 A1 12/2019 Fuerst
2019/0380802 A1 12/2019 Savall
2019/0380809 A1 12/2019 Fuerst
2020/0008901 A1 1/2020 Garcia Kilroy
2020/0015918 A1 1/2020 Payyavula
2020/0022775 A1 1/2020 Garcia Kilroy
2020/0046439 A1 2/2020 Tekiela
2020/0046450 A1 2/2020 Tsao
2020/0069388 A1 3/2020 Bailey
2020/0085522 A1 3/2020 Liao
2020/0113641 A1 4/2020 Itkowitz
2020/0138534 A1 5/2020 Garcia Kilroy
2020/0179068 A1 6/2020 Peine
2020/0194117 A1 6/2020 Krieger
2020/0197112 A1 6/2020 Chin
2020/0197115 A1 6/2020 Vakharia
2020/0205922 A1 7/2020 Cone
2020/0214773 A1 7/2020 Nobles
2020/0214778 A1 7/2020 Turner
2020/0214779 A1 7/2020 Masuda
2020/0222124 A1 7/2020 Savall
2020/0222134 A1 7/2020 Schuh
2020/0275985 A1 9/2020 Thompson
2020/0289212 A1 9/2020 Savall
2020/0289223 A1 9/2020 Denlinger
2020/0330170 A1 10/2020 Farritor
2020/0360096 A1 11/2020 Savall
2020/0360097 A1 11/2020 DiMaio
2020/0390510 A1 12/2020 Thompson
2020/0397517 A1 12/2020 Unsworth
2020/0397529 A1 12/2020 Anderson
2020/0405408 A1 12/2020 Shelton
2020/0405434 A1 12/2020 Schuh
2021/0030495 A1 2/2021 Savall
2021/0052338 A1 2/2021 Hill
2021/0052341 A1 2/2021 Bailey
2021/0059781 A1 3/2021 Peine
2021/0085301 A1 3/2021 Au
2021/0121260 A1 4/2021 Genova
2021/0153964 A1 5/2021 Diolaiti
2021/0153965 A1 5/2021 Lau
2021/0153966 A1 5/2021 Lau
2021/0196411 A1 7/2021 Vakharia
2021/0196413 A1 7/2021 Inoue
2021/0197401 A1 7/2021 Weintraub
2021/0236220 A1 8/2021 Diolaiti
2021/0290326 A1 9/2021 Diolaiti
2021/0290328 A1 9/2021 Miller
2021/0298855 A1 9/2021 Thompson
2021/0304639 A1 9/2021 Ho
2021/0322117 A1 10/2021 Liao
2021/0322119 A1 10/2021 Hares
2021/0353381 A1 11/2021 Usui
2021/0369365 A1 12/2021 Goswami
2022/0015839 A1 1/2022 Savall

(56) References Cited

U.S. PATENT DOCUMENTS

| | | | |
|---|---|---|---|
| 2022/0015852 | A1 | 1/2022 | Savall |
| 2022/0031415 | A1 | 2/2022 | Vargas |
| 2022/0047345 | A1 | 2/2022 | Choi |
| 2022/0096189 | A1 | 3/2022 | Popovic |
| 2022/0184823 | A1 | 6/2022 | Bonny |
| 2022/0192763 | A1 | 6/2022 | Fuerst |
| 2022/0202437 | A1 | 6/2022 | Overmyer |
| 2022/0211452 | A1 | 7/2022 | Clark |
| 2022/0218418 | A1 | 7/2022 | Jolaeimoghaddam |
| 2022/0226056 | A1 | 7/2022 | Beckman |
| 2022/0265380 | A1 | 8/2022 | Bailey |
| 2022/0361736 | A1 | 11/2022 | Danna |
| 2022/0361970 | A1 | 11/2022 | Griffiths |
| 2022/0370163 | A1 | 11/2022 | Schuh |
| 2022/0378526 | A1 | 12/2022 | Balicki |
| 2022/0378527 | A1 | 12/2022 | Basafa |
| 2022/0378533 | A1 | 12/2022 | McDiarmid |
| 2022/0387131 | A1 | 12/2022 | Anderson |
| 2022/0395346 | A1 | 12/2022 | Ihara |
| 2022/0401162 | A1 | 12/2022 | Unsworth |
| 2023/0028689 | A1 | 1/2023 | Rabindran |
| 2023/0045591 | A1 | 2/2023 | de la Fuente Klein |
| 2023/0149105 | A1 | 5/2023 | Thornycroft |
| 2023/0301738 | A1 | 9/2023 | Thompson |
| 2023/0355261 | A1 | 11/2023 | Yu |

FOREIGN PATENT DOCUMENTS

| | | | |
|---|---|---|---|
| DE | 102010009065 | A1 | 8/2011 |
| DE | 102014006264 | A1 | 11/2015 |
| EP | 2845556 | A1 | 3/2015 |
| EP | 3245975 | A1 | 11/2017 |
| EP | 3424651 | A1 | 1/2019 |
| EP | 3459429 | A1 | 3/2019 |
| EP | 3574860 | A1 | 12/2019 |
| EP | 3852668 | | 7/2021 |
| JP | 20130034835 | A | 2/2013 |
| JP | 2013049121 | | 3/2013 |
| JP | 2013510671 | | 3/2013 |
| JP | 2013510672 | | 3/2013 |
| JP | 2016512733 | | 5/2016 |
| JP | 2016514492 | | 5/2016 |
| JP | 2017099820 | | 6/2017 |
| JP | 2019536556 | | 12/2019 |
| JP | 2020529237 | | 10/2020 |
| JP | 2021162200 | A | 10/2021 |
| WO | 20048504 | A2 | 8/2000 |
| WO | 2013018861 | | 2/2013 |
| WO | 2013071071 | A1 | 5/2013 |
| WO | 2014106869 | A1 | 7/2014 |
| WO | 2014151621 | A1 | 9/2014 |
| WO | 2016053657 | A1 | 4/2016 |
| WO | 2016171757 | A1 | 10/2016 |
| WO | 2016201207 | A1 | 12/2016 |
| WO | 2017094844 | A1 | 6/2017 |
| WO | 2018104252 | A1 | 6/2018 |
| WO | 2018107062 | A1 | 6/2018 |
| WO | 2019027922 | | 2/2019 |
| WO | 2019050878 | A2 | 3/2019 |
| WO | 2019099584 | A1 | 5/2019 |
| WO | 2019103954 | A1 | 5/2019 |
| WO | 2019220407 | A1 | 5/2019 |
| WO | 2019220408 | A1 | 5/2019 |
| WO | 2019220409 | A1 | 5/2019 |
| WO | 20200092170 | A1 | 10/2019 |
| WO | 2019240825 | A1 | 12/2019 |
| WO | 2020139405 | A1 | 7/2020 |
| WO | 2020153411 | A1 | 7/2020 |
| WO | 2021141920 | A1 | 7/2021 |
| WO | 2021188127 | A1 | 9/2021 |
| WO | 2022155067 | A1 | 7/2022 |

OTHER PUBLICATIONS

International Search Report and Written Opinion received for PCT Serial No. PCT/IB2022/051286 on Jun. 7, 2022, 13 pgs.

International Search Report and Written Opinion received for PCT Serial No. PCT/IB2022/051293 on Apr. 8, 2022, 16 pgs.

International Search Report and Written Opinion received for PCT Serial No. PCT/IB2022/051321 on Jun. 8, 2022, 16 pgs.

International Search Report and Written Opinion received for PCT Serial No. PCT/IB2022/051328 on Jun. 13, 2022, 16 pgs.

International Search Report and Written Opinion received for PCT Serial No. PCT/IB2022/051279 on Jun. 13, 2022, 15 pgs.

International Search Report and Written Opinion received for PCT Serial No. PCT/IB2022/051244 on Jun. 7, 2022, 13 pgs.

Chinese Search Report received for CN Application No. 2022800288990, receive on Mar. 28, 2026, 13 pgs.

* cited by examiner x1
P1
$\pi_1$
q1
x2
P2
(a)
z1
P1
z2
P2
(b)
P2
x2
P1'
P2'
OJ
d3
x1
P1
(c)
P2
x2
OJ
x1
d4
P1
(d)

METHOD FOR VERIFYING THE INTEGRITY OF A MASTER DEVICE OF A MASTER-SLAVE ROBOTIC SYSTEM FOR MEDICAL OR SURGICAL TELEOPERATION AND RELATED ROBOTIC SYSTEM

CROSS-REFERENCE TO RELATED APPLICATIONS

The present application is a National Stage Filing of PCT International Application No. PCT/IB2022/051286 filed on Feb. 14, 2022, which claims priority to Italian Patent Application No. 102021000003488, filed on Feb. 16, 2021, which is incorporated herein by reference in its entirety.

TECHNOLOGICAL BACKGROUND OF THE INVENTION

Field of Application

The present invention relates to a method for verifying the structural and/or functional integrity of a master device of a master-slave robotic system for medical or surgical teleoperation, and a corresponding master-slave robotic system for medical or surgical teleoperation equipped so as to perform the aforesaid method.

Description of the Prior Art

In the context of robotic teleoperated surgery, with regard to master-slave robotic systems for medical or surgical teleoperation, it is very important to assess whether the master device is functioning well or is intact in structural terms, and to verify whether the position, orientation and opening/closing measurements used to control the slave device are consistent.

This need is particularly felt in the context of unconstrained master devices, which are detected magnetically, optically or with other tracking methods, in which however disturbances or bad detection certainly cannot be excluded, but this need can also emerge in the context of master devices with mechanically constrained interface. Some examples of master devices mechanically unconstrained to the robotic system console, i.e., unconstrained master devices, or "ungrounded" or "flying", are shown for example in documents WO-2019-220407, WO-2019-220408, WO-2019-220409 on behalf of the same Applicant, as well as for example in document U.S. Pat. No. 8,521,331.

In particular, in case of unconstrained master devices detected by means of optical and/or magnetic tracking systems, the need is felt to identify anomalies in reading the master position and/or orientation, and the possibility that external disturbances may compromise the relationships between global and local reference triples.

Furthermore, for all types of master devices, the need is felt to monitor the structural integrity of the master device joints.

Master-slave robotic systems for medical or surgical teleoperation do not provide fully satisfactory solutions to the aforesaid needs, especially taking into account the very stringent safety requirements which derive from the fact that any structural or functional anomaly of the master device, in particular unconstrained, can determine consequent anomalies in the operation of the slave device and the surgical instrument associated therewith, intended to act on the patient, with possible risks.

Therefore, in this context, the need is strongly felt to apply procedures for verifying the functional integrity of the master device, conducted automatically by the control system of the robot for medical or surgical teleoperation, which are efficient and reliable, in order to meet the stringent safety requirements which are required by such applications.

SUMMARY OF THE INVENTION

It is the object of the present invention to provide a method for verifying the structural and/or functional integrity of a master device of a master-slave robotic system for medical or surgical teleoperation, which allows at least partially overcoming the drawbacks mentioned above with reference to the prior art, and responding to the needs particularly felt in the technical field considered.

It is another object of the present invention to provide a method for managing anomalies of a master device comprising carrying out the method for verifying the integrity of the master device.

It is also an object of the present invention to provide a robotic system for medical or surgical teleoperation equipped to perform the control method.

BRIEF DESCRIPTION OF THE DRAWINGS

Further features and advantages of the system and method according to the invention will become apparent from the following description of preferred embodiments, given by way of indicative, non-limiting examples, with reference to the accompanying drawings, in which.

DETAILED DESCRIPTION

Figure 1:
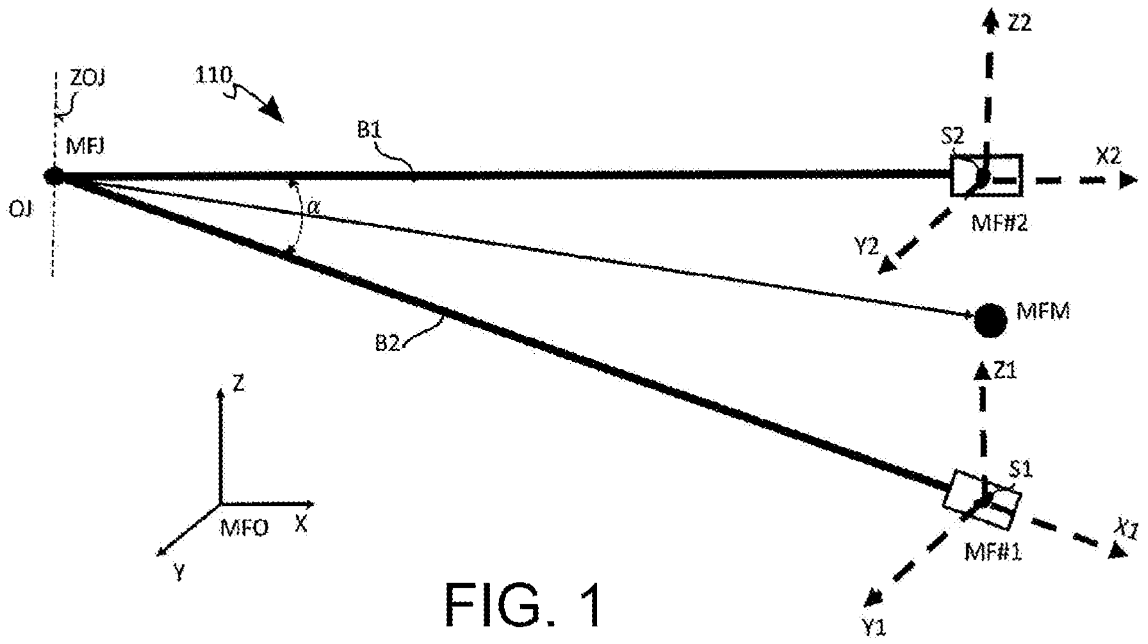
FIGS. 1-8 show the main geometric and physical parameters used for some structural integrity checks of some embodiments of a master device, provided by some embodiments of the method of the invention.

With reference to FIGS. 1-16, a method is described for verifying the structural and/or functional integrity of a master device, which is hand-held and unconstrained, used to control a robotic system for medical or surgical teleoperation, in which such a master device comprises a body comprising two rigid parts constrained to relatively rotate and/or translate with respect to a common axis. For example, such two rigid parts may be constrained in a rotational joint to rotate about the joint axis; or such two rigid parts may be constrained in a prismatic joint to translate along the joint axis, or may be in a roto-translational relationship.

The method comprises the step of measuring and/or detecting the position vectors of at least two points (hereinafter, such two points and the position vectors which uniquely represent them, given a reference frame or coordinate system, will be referred to as P1 and P2), each belonging to one respective of the aforesaid two rigid parts of the master device, and measuring and/or detecting the evolution over time of the said at least two position vectors.

The method further comprises the step of measuring and/or detecting an orientation of each of said at least two points, in which each orientation is expressed as a respective set of three numbers, and measuring and/or detecting the evolution over time of said orientations.

The method then includes defining one or more constraints imposed by constructional or structural features of the master device, deriving from the difference between the number of degrees of freedom necessary to define the state of the master device and the number of information items detected, in which each constraint is associated with a mathematical relation which must be respected in the case of integrity of the master device.

The method then comprises the steps of calculating the mathematical relationships associated with each of the defined constraints, based on the aforesaid detected and/or measured position vectors and orientations and the respective evolutions over time; and finally determining a state of structural and/or functional integrity or non-integrity of the master device, based on a verification of whether or not the mathematical relations associated with each of the constraints defined are respected, utilizing the detected information related to the degrees of freedom that are redundant with respect to the information necessary to determine the state of the master device.

In accordance with an embodiment, the method includes verifying the structural integrity of the master device.

According to an implementation option of such an embodiment, information or conclusions about the functional integrity, i.e., regarding the correctness and adequacy of operation, of the master device are derived from the structural integrity verification.

According to an embodiment, the method is applied to a robotic system for medical or surgical teleoperation comprising the aforesaid master device, at least one slave device and a control unit.

The master device is mechanically ungrounded and adapted to be hand-held by a surgeon during surgery, and is configured to detect a manual command of the surgeon and generate a respective first electrical command signal.

The at least one slave device, or slave robotic assembly, comprises at least one slave surgical instrument configured to operate on the anatomy of a patient, in a manner controlled by the master device.

The control unit provided with a computer is configured to receive the aforesaid first electrical command signal from the master device, generate a second electrical command signal, based on the first electrical command signal, and provide the second electrical command signal to the slave robotic assembly, to actuate the at least one slave surgical instrument.

The control unit is operatively connected to one or more sensors S1, S2, configured to perform the aforesaid detecting and/or measuring steps (for example located at the aforesaid points P1 and P2, respectively).

Furthermore, the control unit is configured to receive and process third electrical control signals representative of the aforesaid detected and/or measured position vectors and of the related evolution over time.

The aforesaid calculating and determining steps are performed by the control unit, in which said one or more constraints and the respective mathematical relations are stored.

In accordance with an embodiment of the method, the aforesaid measuring and/or detecting steps comprise measuring and/or detecting the aforesaid position vectors and the aforesaid orientations, and the related evolutions over time, with respect to a first reference frame (x, y, z), also referred to as "General Master Reference" MFO hereinafter, associated with the robotic system for teleoperated surgery, and having predetermined axes and origin at a preset point.

According to an implementation option, in which the method is performed in a robotic system for teleoperated surgery comprising an operating console, the aforesaid first reference frame (or coordinate system) is integral with the robotic system console.

In an embodiment, the aforesaid operating console comprises at least one surgical chair to which said first coordinate system is integral.

In accordance with an embodiment of the method, the aforesaid measuring and/or detecting steps are performed by two or more magnetic sensors. Each of the magnetic sensors is arranged at a respective one of the aforesaid at least two points, belonging to or integral with the master device, and is configured to detect respective local values of a magnetic field generated by a magnetic field generator constrained to a part of the robotic system for surgical or medical teleoperation, In such a case, the aforesaid first reference frame or General Reference System MFO, has its origin at the magnetic emitter, and comprises three orthogonal axes x, y, z.

According to an implementation option of such an embodiment, the robotic system for surgical or medical teleoperation further comprises at least one tracking system which is suitable for detecting the input position and orientation of the master device within a predetermined tracking volume, so that the actuation of the slave surgical instrument depends on the manual command given by the surgeon by means of the master device and/or on the position and orientation of the master device. In such a case, the magnetic field generator belongs to the aforesaid tracking system.

In accordance with another embodiment of the method, the aforesaid measuring and/or detecting steps are performed by at least one optical sensor or camera, associated with and/or constrained to the robotic system for teleoperated surgery. In such a case, said first reference frame MFO is an internal reference frame or coordinate system of the optical sensor or camera.

According to possible implementation options of such an embodiment, the aforesaid at least one optical sensor or camera is constrained to and/or integral with the surgical chair, and/or is mounted on a support wearable by the surgeon, so as to be integral with the surgeon.

In accordance with an embodiment, the method further comprises the step of defining a second reference frame (x1, y1, z1) or MF #1 and a third reference frame (x2, y2, z2) or MF #2, respectively associated with said at least two points of the master device.

Each of said second reference frame (x1, y1, z1) and third reference frame (x2, y2, z2) comprises: a respective origin, corresponding to the respective point; a respective first axis (x1; x2) aligned with the respective rigid part of the master device to which the respective point is associated; a respective second axis (z1, z2) parallel to the rotation axis of the two rigid parts of the master device, or perpendicular to the translation axis of a rigid part of the master device with respect to the other rigid part; a respective third axis (y1; y2) orthogonal to both the first axis and the second axis so as to form a levorotatory set of three axes.

In such a case, the aforesaid step of measuring and/or detecting the position vectors and the related evolution over time comprises measuring and/or detecting the position of the origin, and the related evolution over time, of the second reference frame (x1, y1, z1) and the third reference frame (x2, y2, z2) with respect to the first reference frame (x, y, z); and the aforesaid step of measuring and/or detecting the orientation and/or the related evolution over time, of the second reference frame (x1, y1, z1) and the third reference frame (x2, y2, z2) with respect to the first reference frame (x, y, z).

According to an embodiment of the method, said at least two points belonging to or integral with the master device comprise a tip or free end (or a portion near the tip or free end) of the first rigid part or rigid bar or rigid arm of the master device; and a tip or free end (or a portion near the tip or free end) of the second rigid part or rigid bar or rigid arm of the master device.

The aforesaid rigid parts or bars or arms are articulated to each other or otherwise constrained to rotate and/or translate about a common axis.

In accordance with an embodiment of the method, in which the master device comprises a body comprising two rigid parts constrained to relatively rotate with respect to a common axis, and in which the command given by the surgeon corresponds to a variation of the opening angle between said two rigid parts, the method comprises the further step of calculating the positional set of three numbers and rotational set of three numbers of a reference point and the opening angle of the master device, based on the aforesaid detected vectors.

According to several possible implementation options, the aforesaid reference point comprises one of the following points:

- midpoint between the two tips; and/or
- center of gravity of the master device; and/or
- master device joint.

In accordance with another embodiment of the method, in which the master device comprises a "pen" body comprising two rigid parts constrained to translate with respect to each other (or translational/prismatic joint) on a direction coinciding with a longitudinal extension of the master device body, the aforesaid two rigid parts being integral with each other in rotations about the longitudinal extension of the master device body, and in which the command given by the surgeon corresponds to a translation of the rigid part with respect to the other, the method comprises the further step of calculating the positional set of three numbers and the rotational set of three numbers of a first sensor associated with a first reference point on the first rigid part, and of a second sensor associated with a second reference point on the second rigid part, based on the aforesaid detected vectors. Such an embodiment is diagrammatically shown in FIG. 11 and FIG. 15.

According to an implementation option, the sensors are arranged as co-linear in this case. Therefore, in this case, the geometric integrity constraints then verify that the sensors are co-linear and not relatively rotated with respect to the zero position.

According to an implementation option, the seats of the "pen" master device body receiving the sensors have appropriately oriented abutment surfaces for positioning the sensors in a repeatable and predeterminable manner.

In accordance with an embodiment of the method, the two rigid parts or arms are in a roto-translational relationship about a common axis, for example they form a cam.

Elastic elements may be provided between the two rigid parts of the master device.

In accordance with an embodiment of the method, the step of determining a state of integrity comprises confirming the state of integrity if all the defined constraints are respected, within predetermined tolerance limits; and identifying a state of non-integrity if at least one of the defined constraints is not respected, even after taking into account the predetermined tolerance limits.

Further details on the constraints which must be met to recognize a state of integrity, according to different embodiments of the method, will be provided below by way of example.

According to an embodiment of the method, the aforesaid constraints comprise the following constraint: the detected points corresponding to the aforesaid at least two points (the position vector of which is measured or detected) must lie on the same plane, within a coplanarity tolerance limit, regardless of the mobility of the gripping axis.

According to an implementation option, said coplanarity tolerance limit provides that the distance between each point and the plane defined by the other is less than or equal to 0.5 mm.

According to another embodiment of the method, in which the master device comprises a rotational joint, said constraints comprise the following constraint:

- the detected points (P1, P2) corresponding to the aforesaid at least two points must project always in the same predetermined manner on the orthogonal plane defined by the normal axes (z1, z2), parallel to the joint axis, passing through the two points (P1, P2), or the vector product between the two vectors (x1, x2) joining the rotational joint and the two points, respectively, must always be concordant or discordant with the vector associated with one of said normal axes (z1), in which the concordance or discordance is predetermined based on constructional features of the master device.

According to another embodiment of the method, in which the master device comprises a prismatic joint, said constraints comprise the following constraint:

- the measured points (P1, P2) corresponding to the aforesaid at least two points must project always in the same predetermined manner on the orthogonal plane defined by the axes (y1, y2), coplanar to the master device and perpendicular to the directions defined by the two rigid parts.

This means that the point P2 must lie in the positive half-space of the plane passing through the point p0 and having the axis y2 as normal axis, and vice versa for P1 and y1. According to another embodiment of the method, said constraints comprise the following constraint: the normal axes (z1, z2), parallel to the joint axis, passing through said at least two points (P1, P2) must be parallel and concordant, within a parallelism acceptability limit.

According to an implementation option, said parallelism acceptability limit is defined by a maximum acceptable limit of 8° of the angle defined by said axes (z1, z2).

According to another embodiment of the method, the aforesaid constraints comprise the following constraint: considering the pairs (P1,x1), (P2,x2) consisting of each of the two points and the respective axis joining the point to the joint, and translating each point along the corresponding axis by a linear metric quantity (L), two respective translated points (P1', P2') are obtained, which must be distanced by a distance less than a maximum allowed distance between translated points.

According to an implementation option, the aforesaid maximum distance allowed is 1 cm, for a master device with a rotational joint, and is equal to the distance between the two points (P1, P2) at less than a 0.5 cm margin, for a master device with a prismatic joint.

With reference to the aforesaid embodiment, it should be noted that the constitution of the arms, of known length, and hinged at a point OJ requires that if we move the aforesaid first point P1 along the line representing the first arm, for a length equal to the known length of the arm (axis x1), we must reach a point corresponding to the joint OJ; similarly, if we move the aforesaid second point p2 along the line representing the second arm (axis x2), for a length equal to the known length of the arm, we must reach a point corresponding to the same joint OJ.

According to another embodiment of the method, said constraints comprise the following constraint: the distance d between the at least two points (the position vectors of which are detected or measured) cannot exceed the distance at which the aforesaid at least two points are, under maximum opening conditions of the master device, and, where applicable, such a distance cannot be less than the minimum distance measured at the minimum opening of the master device.

It should be noted that the aforesaid maximum opening of the master device and minimum opening of the master device are predetermined parameters, depending on constructional features of the master device.

In accordance with an embodiment of the method, all the quantities associated with the aforesaid constraints are either detected (for example the positions of the two tips) or calculated (for example planes, lines, distances) in real time, by virtue of the measurements performed which provide the 12 degrees of freedom, of which 5 are redundant.

The verification that said constraints are respected or not is carried out in real time.

If at least one of the constraints is not respected, the anomaly is detected in real time.

In accordance with an embodiment of the method, all of the aforesaid constraints are taken into account for verification.

In accordance with an embodiment of the method, the structural integrity of the master device is verified, based on the verification of one or more of the aforesaid constraints.

According to an implementation option, the method further includes detecting disturbances and/or distortions of the tracking field (i.e., for example, the electromagnetic field generated by the aforesaid tracking system), based on the verification of one or more of the aforesaid constraints.

In such a case, by virtue of the step of determining a state of integrity or non-integrity of the master device based on a verification of whether or not the mathematical relations associated with each of the defined constraints are respected, it is possible to identify the presence of external disturbances which distort the tracking field, since the detection of an abnormal mathematical relation between the sensors can be due to a disturbance which distorts the tracking field and not to a real structural breakage of the master device. In other words, in this case, the mathematical constraint between the sensors is broken because of a functional abnormality of non-integrity due to an unwanted disturbance of the tracking field.

According to an embodiment of the method, the step of verifying the functional integrity of the master device is performed by further providing the step of detecting/quantifying the noise associated with the detection of the instantaneous position vector to define the instantaneous acceptability threshold.

For example, by detecting/quantifying the noise associated with the detection of the instantaneous position vector with a magnetic tracking system, information is provided on possible perturbations from an external magnetic field.

Also comprised in the present invention there is a method for managing anomalies of a master device comprising carrying out the method for verifying structural integrity, according to any of the previously described embodiments.

In such a method, any non-compliance with the constraint involves the immediate interruption of the teleoperation and of the movements of the surgical instrument associated with the slave device.

According to an implementation option, the aforesaid method further comprises the steps of providing information about the outcome of the verification to the robotic system control system, and/or communicating the information obtained to Robotic System State Machine, and/or User Interface and/or Slave-side Endpoint.

A robotic system for medical or surgical teleoperation comprising a master device, at least one slave device and a control unit is now described.

The master device is unconstrained, i.e., mechanically ungrounded, and intended to be hand-held by a surgeon during surgery, and is configured to detect a manual command of the surgeon and generate a respective first electrical command signal. The master device comprises a body comprising two rigid parts (B1, B2; 1180, 1190; 1380, 1390; 1480, 1490; 1580, 1590; 1680, 1690) constrained to relatively rotate and/or translate with respect to a common axis (ZOJ; X-X).

The at least one slave device, or slave robotic assembly, comprises at least one slave surgical instrument configured to operate on the anatomy of a patient, in a manner controlled by the master device.

The control unit provided with a computer is configured to receive the aforesaid first electrical command signal from the master device, generate a second electrical command signal, based on the first electrical command signal, and provide the second electrical command signal to the slave robotic assembly, to actuate the at least one slave surgical instrument.

The system is configured to perform the following actions:

- measuring and/or detecting the position vectors (P1, P2) of at least two points, each of which belonging to a respective one of the aforesaid two rigid parts (B1, B2; 1180, 1190; 1380, 1390; 1480, 1490; 1580, 1590; 1680, 1690) of the master device, and measuring and/or detecting the evolution over time of said at least two position vectors;
- measuring and/or detecting an orientation of each of the aforesaid at least two points, each orientation being expressed as a respective set of three numbers, and measuring and/or detecting the evolution over time of such orientations;
- defining one or more constraints, or storing one or more predetermined constraints, such constraints are imposed by constructional or structural features of the master device, deriving from the difference between the number of degrees of freedom necessary to define the state of the master device and the number of information items detected, each constraint is associated with a mathematical relation which must be respected in the event of integrity of the master device;

calculating the mathematical relations associated with each of the constraints defined, based on the detected and/or measured position vectors and orientations and on the respective evolutions over time;

determining a state of structural and/or functional integrity or non-integrity of the master device, based on a verification of whether or not the mathematical relations associated with each of the constraints defined are respected, utilizing the detected information related to the degrees of freedom that are redundant with respect to the information required to determine the state of the master device.

According to an embodiment of the system, the aforesaid control unit is operatively connected to one or more sensors S1, S2 configured to perform the aforesaid detecting and/or measuring steps.

According to an implementation option, the control unit is further configured to receive and process third electrical control signals representative of the aforesaid detected and/or measured position vectors and of the related evolution over time.

According to an implementation option, the aforesaid one or more constraints and the respective mathematical relationships are stored in the control unit, and the control unit is further configured to perform the aforesaid calculating and determining steps.

According to different embodiments, the system is configured to perform a method for verifying the structural integrity of a master device according to any of the embodiments disclosed in the present description.

According to an embodiment of the system, the master device body is disposable and thus typically made of plastic. The parts forming the joint can be made of disposable plastic.

According to an implementation option, the master device body delimits seats for receiving respective sensors, and such seats comprise appropriately oriented sensor abutment surfaces so that the positioning of the sensors with respect to the master device body is predeterminable and repeatable, with the aim of detecting the mutual orientation of the sensors.

According to several possible implementation options (corresponding to implementation options of the method already disclosed above), if the joint of the master device body is a rotational joint (e.g., hinge) then the geometric constraints are based on the rotation axis, while if the joint is of such a type as to allow translation in a plane, the geometric constraints are based on belonging to a plane.

According to an embodiment, the robotic system for medical or surgical teleoperation is configured to perform a method for managing anomalies of a master device (in turn comprising performing the method for verifying structural integrity), according to any of the previously described embodiments.

With reference to FIGS. 1-16, some embodiments of the method, previously defined in more general terms, will be further detailed below, by way of non-limiting example.

As disclosed above, the present method relates to a broad class of master device interfaces for robotic surgical teleoperation system, characterized by redundant measurements of position and orientation.

In particular, master devices with two parts, or tips, which can be closed with a hinge or hinge joint are considered, for example. Each part is associated with a position measurement, which is directly measured or deducted.

For controlling the slave device, and in particular the surgical instrument (or "end-effector") associated therewith, a master reference coordinate frame (or master reference frame or "Master Frame", MFM) can be defined expressed relative to the master measurement coordinate frame (or "General Master Frame", or "Master Frame Origin", or x,y,z, or MFO).

The position of one or more reference points of the master device, at any time, is then defined with respect to the coordinates of the aforesaid master reference coordinate frame (MFM).

As already noted, in some embodiments, the master reference coordinate frame MFM, and the related position of the master device, is measured directly, for example using an optical marker placed on the master device, at an appropriately chosen point. In this case, the gripping angle of the "gripper" master device is measured with another technique, for example a magnetic encoder.

In other embodiments, where the master device is still of a "gripper" type, with two parts hinged in a joint, the method includes measuring the position of each of the aforesaid two parts (or of the respective tips) of the master device. In such a case, each of the two parts of the master device is associated with a reference frame thereof, i.e., a frame of reference coordinates thereof (indicated here respectively as MF #1 and M F #2), expressed with respect to the origin of the aforesaid General Master Frame MFO.

The coordinate transformations between the Master Frame MFM and the General Master Frame MFO can be expressed by known coordinate transformation techniques starting known from the Master Frames of the parts of the master device, MF #1 and MF #2, by averaging the position and orientations. For some evaluations it may also be useful to introduce an additional Master Frame Joint MFJ reference frame like the Master Frame MFM and positioned at the joint OJ of the master device (see FIG. 10).

The principle shared by the aforesaid various embodiments is that the measurements performed on the two parts of the master device provide 12 degrees of freedom. The 12 degrees of freedom detected are three positions for the first portion of the master device with respect to the General Master Frame; three positions for the second portion of the master device with respect to the General Master Frame; three values representative of the rotation of the first master device coordinate frame MF #1 with respect to the General Master Frame MFO; three values representative of the rotation of the second master device coordinate frame MF #2 with respect to the General Master Frame MFO.

On the other hand, compared to the 12 degrees of freedom measured, the mechanical structure of the master device has only 7 degrees of freedom, which provides 5 degrees of freedom linked to mechanical constraints, and therefore, in principle, provides 5 different mathematical relations (which express such constraints) and which must be respected, so that it can be concluded that the master device is structurally intact.

The verification of such mathematical constraint relations, performed by the method in the different embodiments thereof, thus allows achieving the result of verifying the structural integrity of the master device.

Examples of the constraints which are tested have already been described above, and are disclosed in more detail below, in terms of how they are measured and how they are transformed into a verification of master device integrity.

The examples shown in FIGS. 1-8, 13-14 and 16, refer to a master device 110, 1310, 1410 of the "gripper" type (or "master grip controller") which provides the application of a force by the fingers of the gripping hand more or less halfway between the hinge joint OJ and the tips T1, T2 of the two arms B1, B2 of the gripper (corresponding to the "two parts" of the master device mentioned several times). This type of master device is characterized by a total of 7 degrees of freedom: three of orientation, three of position and the opening between the gripper arms. As already shown, optical and/or magnetic technologies can be used to detect the position of the gripper arms.

In the examples shown below, only the position of the reference points of the arms, where the sensors are located, will be considered in a frame of absolute reference coordinates.

Figure 2:
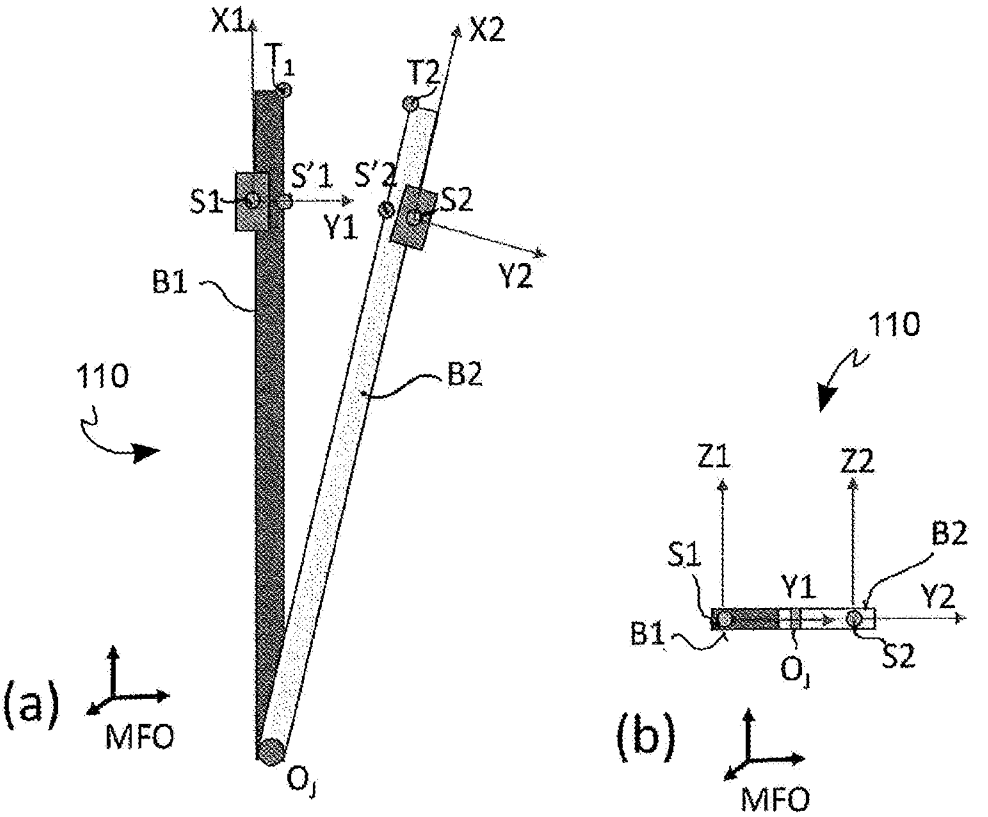

FIGS. 1 and 2 diagrammatically depict a master device 110 with the two sensors S1, S2 arranged near the tips T1, T2 of the arms B1, B2 of the "gripper" body.

In the example in FIG. 1, the hinge joint OJ is on the left at the Master Frame Joint MFJ, and allows a rotation (the angle α between the arms B1 and B2 is shown) of the arms B1 and B2 with an axis ZOJ parallel to the two axes Z1 and Z2 of the two arms B1, B2. The axes X1 and X2 are in the direction of the arms B1 and B2, with a direction away from the joint OJ.

The position and rotation measurements of each of the two sensors S1, S2 can be represented by a three-dimensional position vector (thus obtaining two vectors which we indicate as P1 and P2) and by a rotation matrix for each arm (thus obtaining two rotation matrices). Each sensor S1, S2 is thus associated with respective position and rotation information.

It should be noted that preferably the rotation can be associated with the three-dimensional orthogonal subgroup SO(3) and therefore the number of degrees of freedom in this illustrated example is always 3 (regardless of the type of representation, whether it is based on a rotation matrix with 9 numbers, as exemplified herein, or based on 3 Euler angles, or based on quaternions with four values).

The arrangement (i.e., position and rotation) of the reference points S'1, S'2 (or of the tips T1, T2) of the arms B1, B2 allows calculating a pose or arrangement (i.e., position and rotation) of the entire master device 110, for example with a position calculated as the average PM of the two positions P1 and P2 of the sensors S1, S2, and the rotation as an average of the rotations. The opening angle α of the "gripper" can be calculated using the distances between the tips T1, T2 and the known lengths of the arms B1, B2 of the master device 110, i.e., the known distances between the joint OJ and each of the reference points S'1, S'2 equipped with sensors S1, S2 (assuming that the sensors are placed at equidistant points from the joint OJ, the aforesaid two distances are equal).

Figure 3:
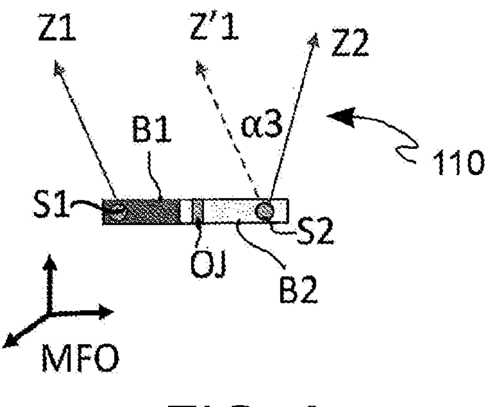
Figure 4:
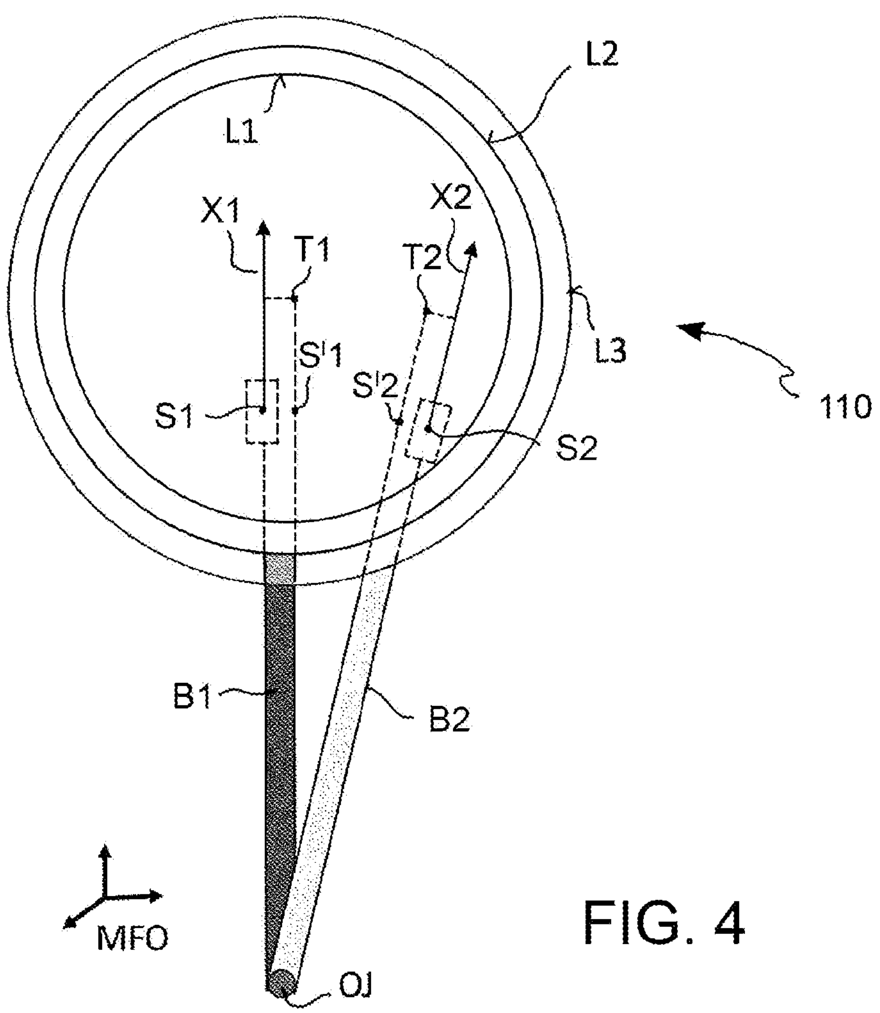
Figure 5:
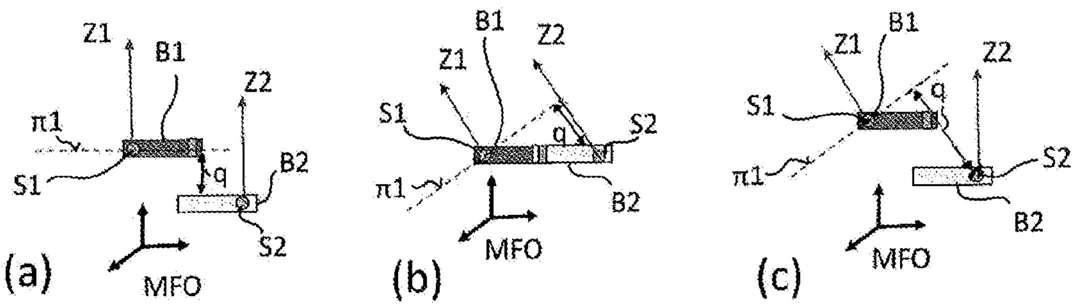
Figure 6:
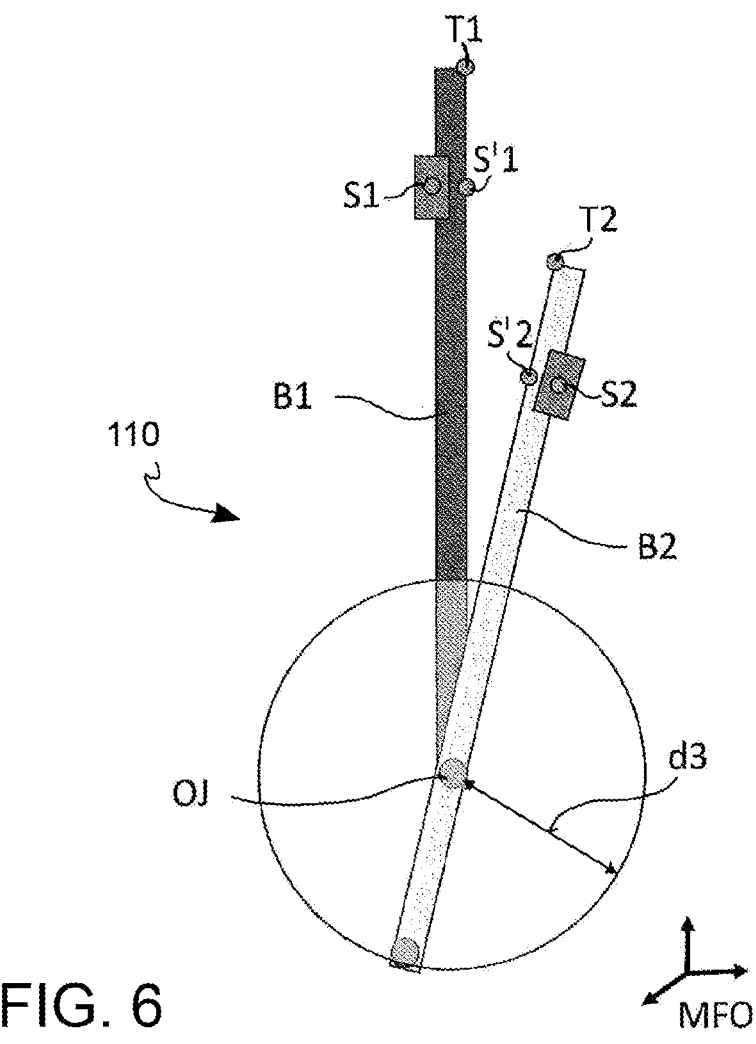

Based on the known value of the joint-sensor distance and the measured average values (average of the positions, average of the rotations) and the angle α, in order to precisely define the constraints to be verified, the following parameters are calculated in the example shown here:

Parameter 1: planarity between the axes Z1 and Z2, measured in degrees (for example as shown in FIG. 3 where the angle α3 is the angle between the axes Z1 or the image thereof Z1' translated into P2 and Z2);

Parameter 2: maximum distance (d) between the sensors, measured in mm (for example, FIG. 5 diagrammatically shows various strategies for calculating said maximum distance d based on the relative orientation of the axes Z1 and Z2);

Parameter 3: distance between the reference frame origin of a sensor (S1: MF #1 or S2: MF #2) and the plane of the other sensor, measured in mm;

Parameter 4: distance between the two lines of the arms of the master device, measured in mm.

On this basis, for example, the following principle constraints are defined as follows.

1. Points P1 and P2 belong to the same plane; in particular, the plane π1 defined by point P1 and axis Z1 contains point P2, and the plane defined by point P2 and axis Z2 contains point P1.
2. The normal axes Z1 and Z2 must be parallel.
3. The further points P1' and P2' which are obtained by moving points P1 and P2 backwards on the arms by a known length must both coincide with the point OJ which corresponds to the joint and the origin of the Master Frame Joint MFJ reference frame.
4. The opening of the "gripper" must be below a maximum value, as well as the maximum distance between the two points P1 and P2.

Figure 8:
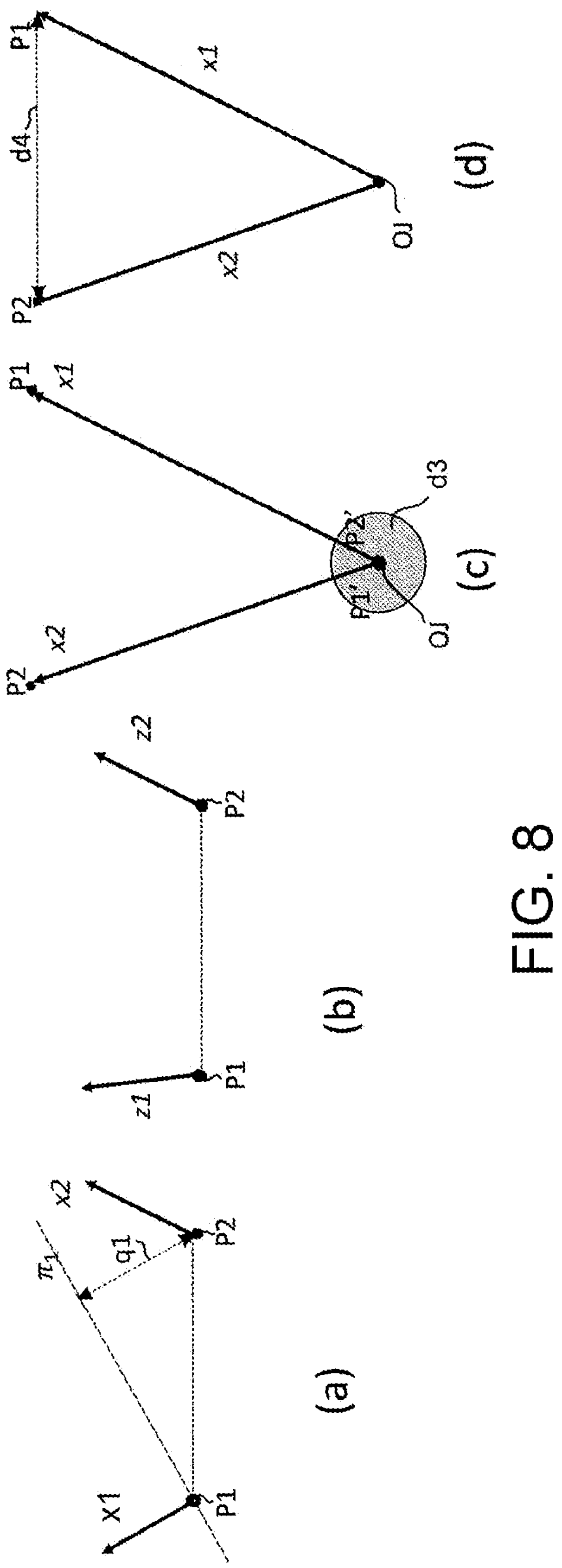

In practice, the aforesaid theoretical constraints must be relaxed taking into account tolerances, due to constructional imperfections and measurement errors, leading to the following respective practical criteria, as shown for example in FIG. 8, a-d:

1. (FIG. 8-*a*) the plane (π1: P1,x1) must contain the point P2 within a certain tolerance, which is expressed by verifying that the absolute distance q between P2 and the plane (π1: P1, z1) is below a given threshold q1; similarly, for point P1 with respect to the plane (P2, z2);
2. (FIG. 8-*b*) the scalar product between z1 and z2 must have a minimum value, which corresponds to a predefined maximum angle of orientation difference;
3. (FIG. 8-*c*) the distance between the further points P1' and P2' (as defined above) must be less than a given threshold d3;
4. (FIG. 8-*d*) the distance d4 between points P1 and P2 must be below the physical limit plus a certain threshold.

Each of the aforesaid criteria, associated with the various constraints, is associated with a parameter detectable in real time and a relation which can be calculated in real time, which is used for a real-time estimate about the structural integrity of the master device.

If anomalies are detected, it is also possible to recognize the type of anomaly.

Figure 7:
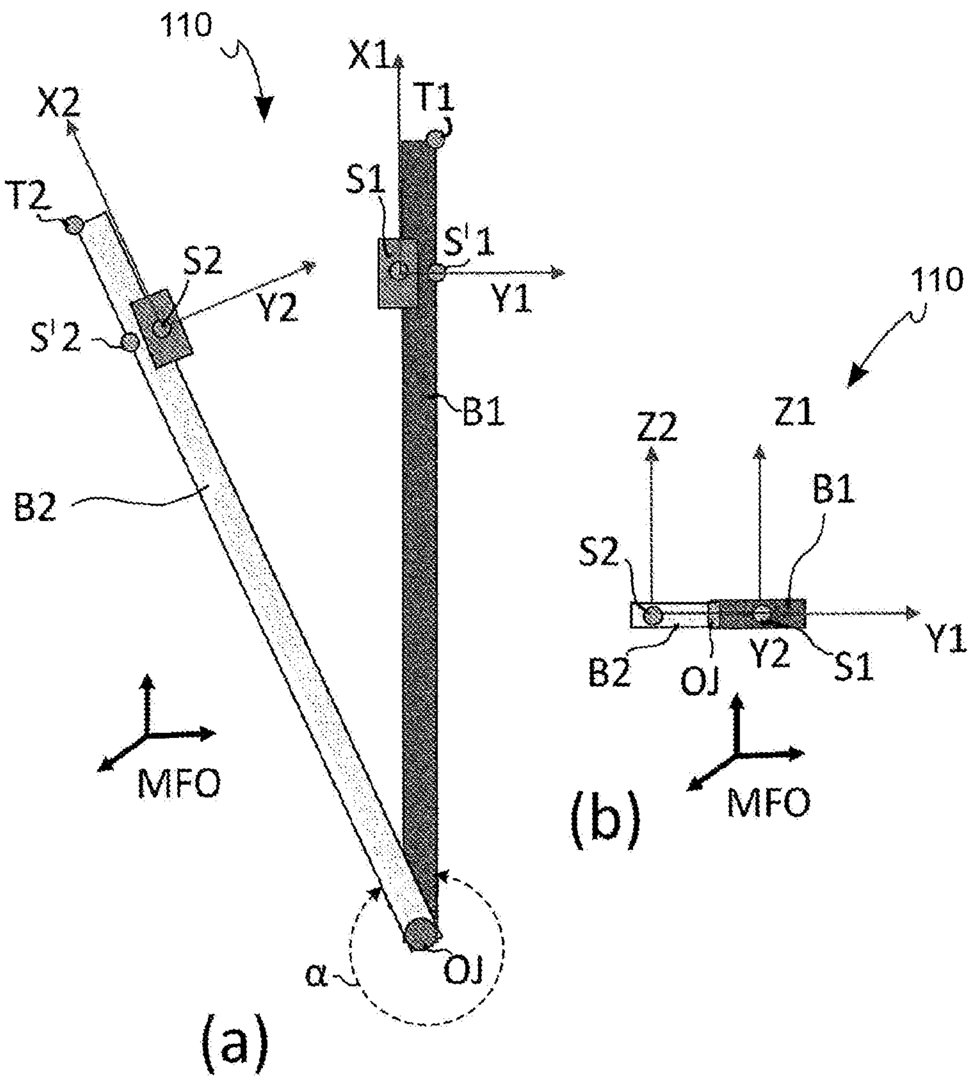

FIGS. 4-7 show, by way of example, situations corresponding to some detectable anomalies, i.e., respectively, maximum distance L1, L2, L3 not to be exceeded (FIG. 4, where in the example shown the distances L1: expected distance between the sensors in a resting configuration, L2: maximum distance allowed between the sensors in a resting configuration, L3: threshold distance between the sensors indicative of structural damage); angles between the axes Z1 and Z2 (FIG. 5*a*-*c*); intersection of the two arms (FIG. 6); inversion between right and left arm (FIG. 7).

According to an implementation option, given that the measurement system may be subject to errors and considering that any structural problems of integrity of a master device are persistent over time, it may be useful to introduce an evaluation over time of the information received from the identification system.

Such an evaluation over time can be entered downstream of the first non-temporal level. For example, a floating window evaluation can be used with a recognition threshold (for example, 60% structural errors over a 100 ms window).

Figure 9:
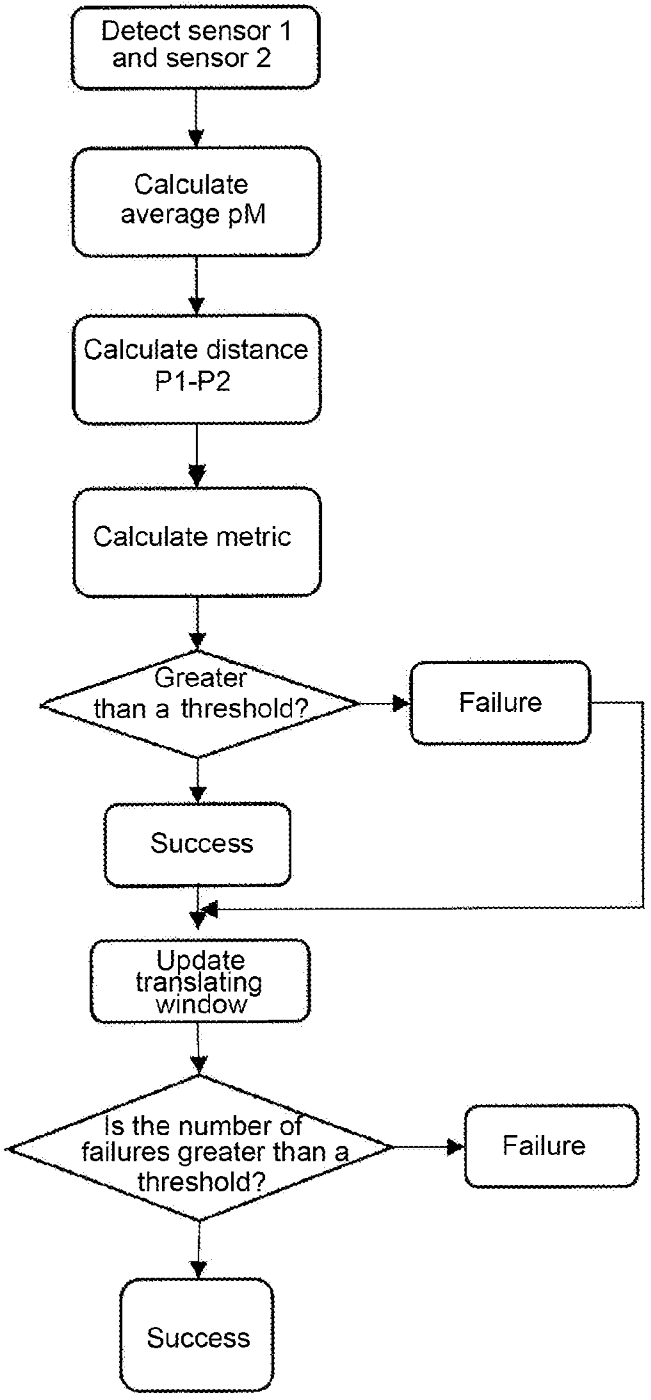
FIG. 9 is a flowchart showing an embodiment of the method of the invention.
Figure 10:
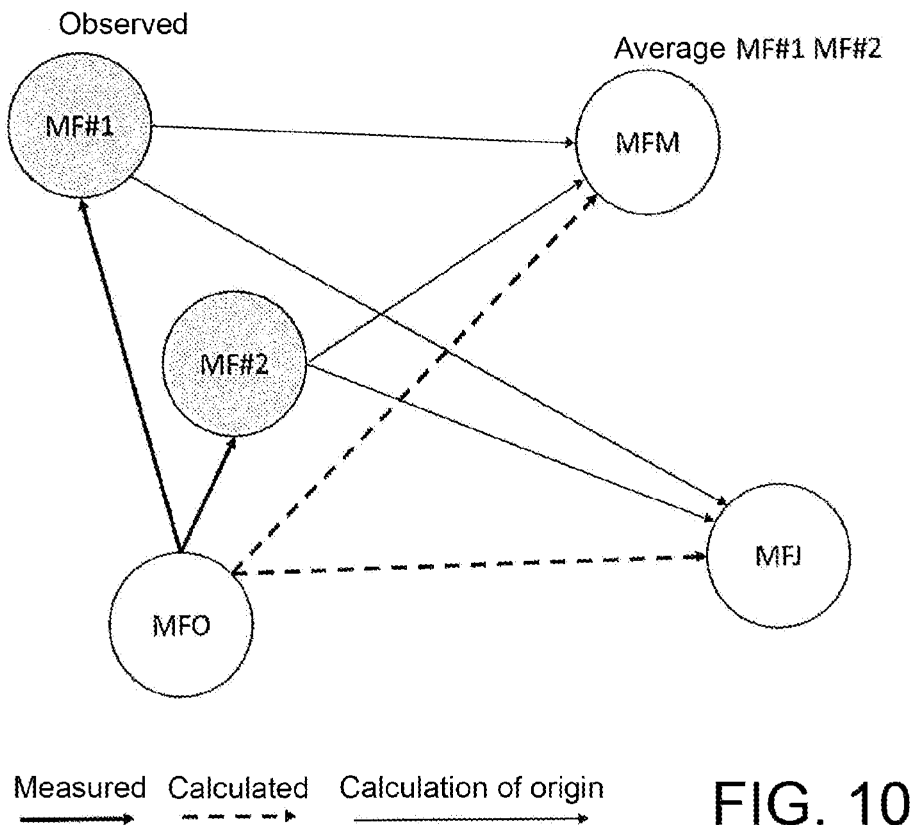
FIG. 10 diagrammatically shows a map of the reference frames, adopted in an embodiment of the method.

According to an embodiment, the combination of the identification algorithm with the evaluation over time is illustrated in the flowchart shown in FIG. 9. The choice of parameters involved in such an evaluation over time can be based on the safety consideration of the specific teleoperation system, evaluating the maximum acceptable time for an invalid movement of the surgical instrument of the slave device.

Figure 12:
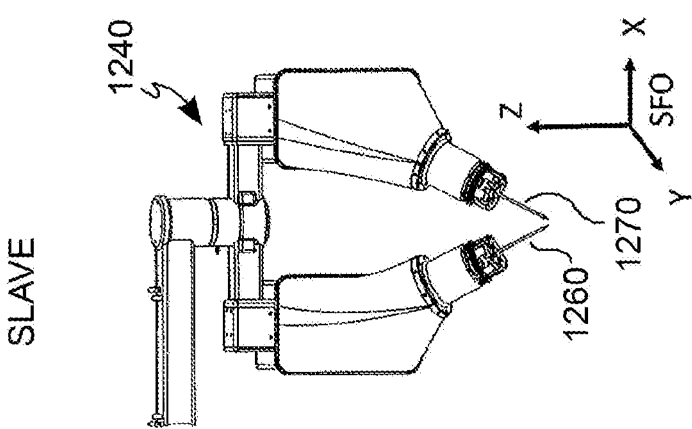
FIG. 12 diagrammatically shows a robotic system for surgical teleoperation, according to an embodiment.
Figure 12:
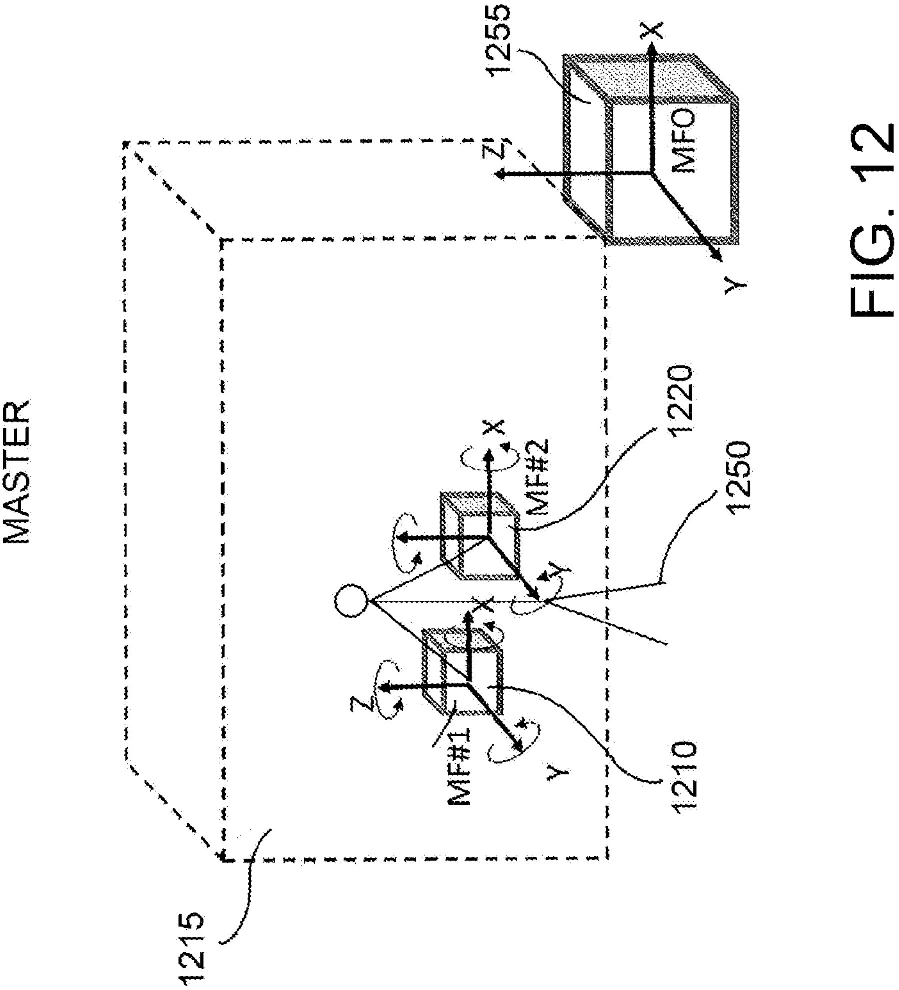

In the embodiment illustrated in FIG. 12, a teleoperated robotic surgery system 1200 is shown which comprises at least one unconstrained master device 410, 420 having an assigned workspace 415, 425 (in the example shown, two unconstrained master devices 1210, 1220 are diagrammatically shown held by a surgeon 1250), a control unit, shown here as belonging to a console 1255, and a slave device 1240 (in the illustrated example, two slave surgical instruments 1260, 1270 are shown).

Figure 13:
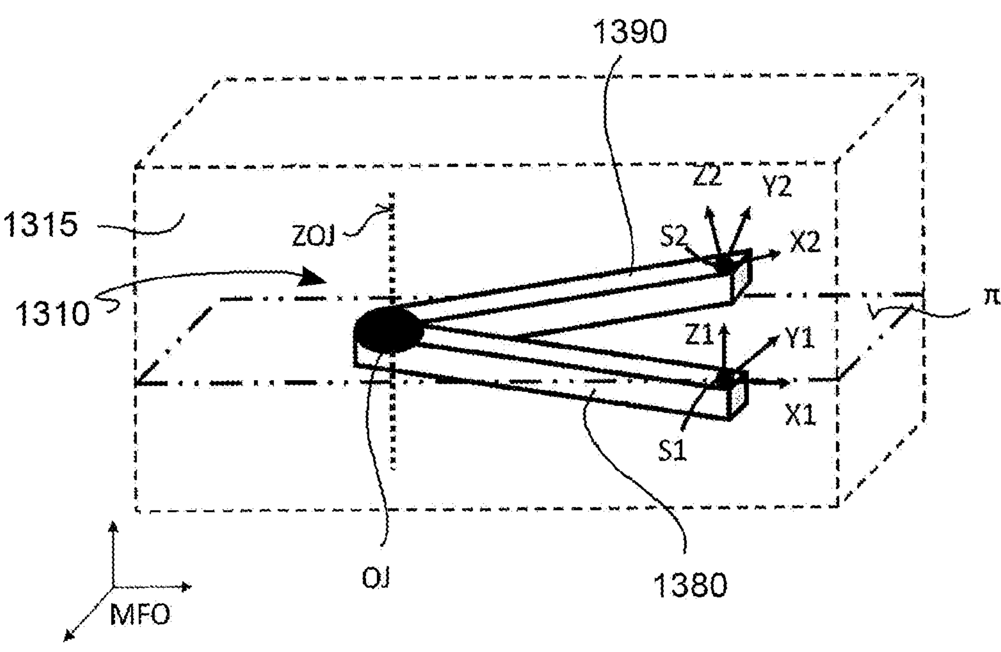
FIGS. 13 and 14 diagrammatically show some integrity checks of a master device according to an embodiment of the method.

FIG. 13 shows an embodiment of an unconstrained master device 1310 within the workspace 1315 assigned thereto, in which the body of the master device 1310 is formed by two rigid parts 1380, 1390 constrained to rotate about a common axis ZOJ, in which verifying the integrity includes verifying the coplanarity of the two sensors S1 and S2, i.e., whether both sensors S1, S2 lie on a plane π (in the illustrated example, the sensors S1, S2 are shown non-coplanar, indicative of an anomaly condition).

Figure 14:
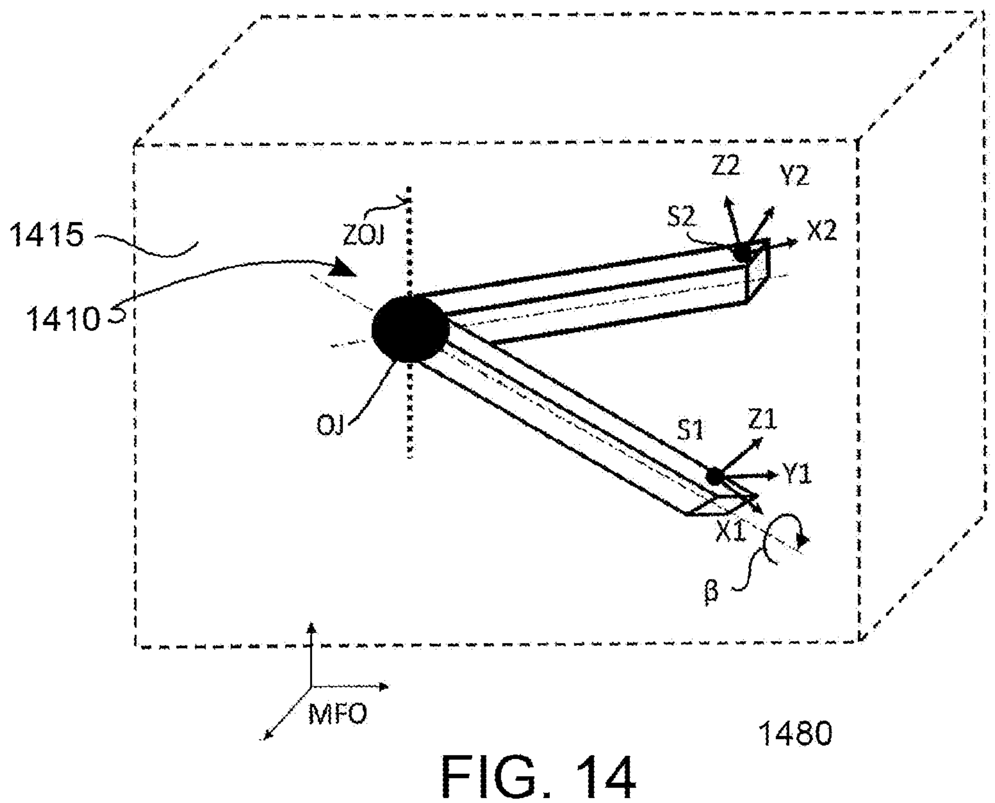

FIG. 14 shows an embodiment of an unconstrained master device 1410 within the workspace 1415 assigned thereto, in which the body of the master device 1410 is formed by two rigid parts 1480, 1490 constrained to rotate about a common axis ZOJ, in which verifying the integrity includes verifying a parallelism condition of the two sensors S1, S2 (in the illustrated example the rigid part 1480 is rotated about the longitudinal axis X1 thereof by an angle β, and therefore the sensors S1 and S2 are not parallel to each other, which is indicative of an anomaly condition).

Figure 16:
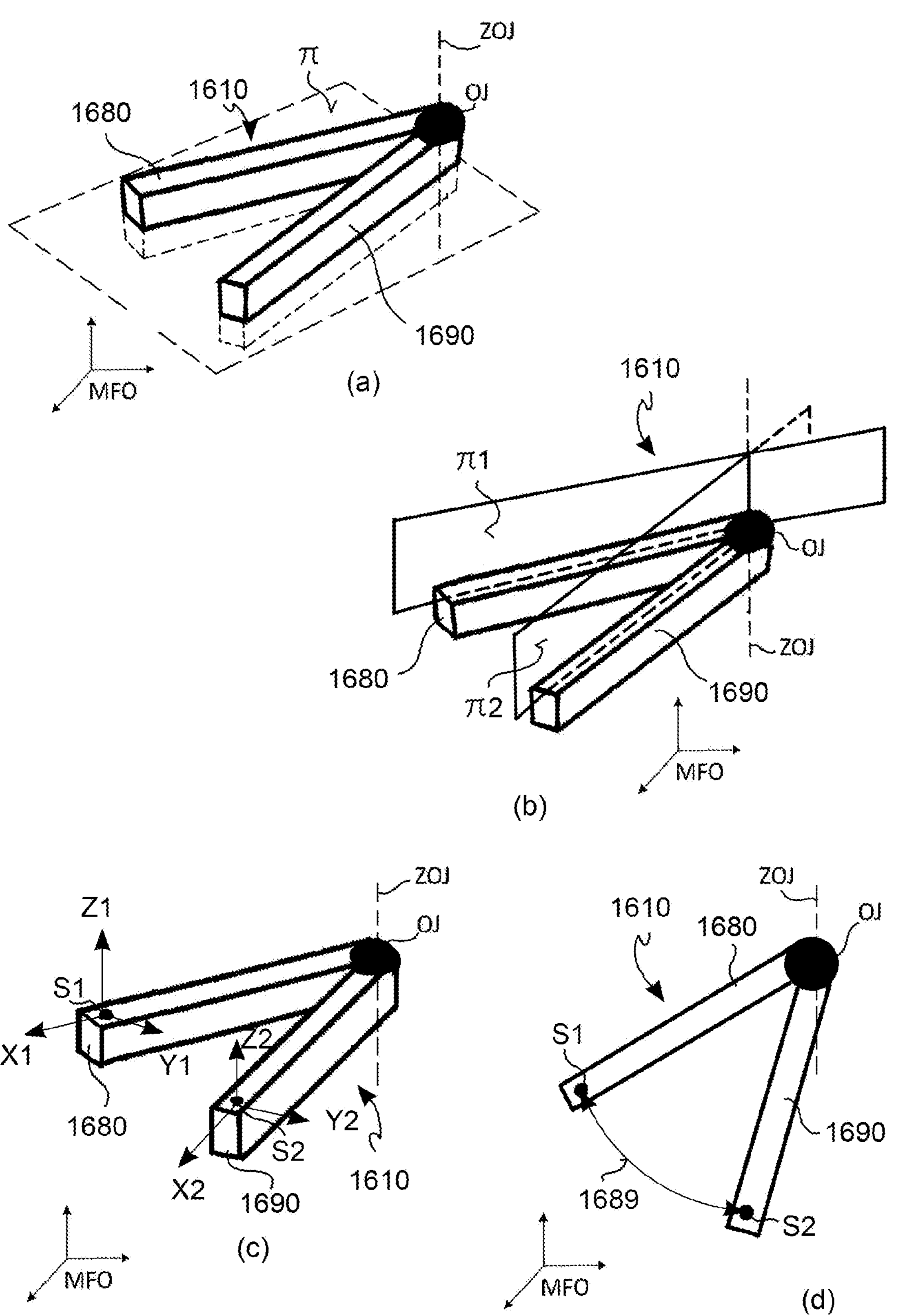
FIG. 16*a-d* diagrammatically show some integrity checks of a master device according to an embodiment of the method.

FIG. 16 diagrammatically shows an unconstrained master device 1610 having a body formed by two rigid parts 1680, 1690 constrained to rotate about a common axis ZOJ, in which verifying the integrity includes verifying: (a) that the two rigid parts 1680, 1690 lie in a plane π, (b) that the planes π1, π2 identified by the two rigid parts 1680, 1690 and preferably by the sensors S1, S2 associated therewith are parallel to each other and incident in the axis ZOJ of the joint OJ, (c) that the sensors S1, S2 are in a predetermined mutual configuration, (d) that the opening/closing trajectory defined by the two sensors S1, S2 corresponds to a predetermined trajectory diagrammatically shown with the curve 1689.

Figure 11:
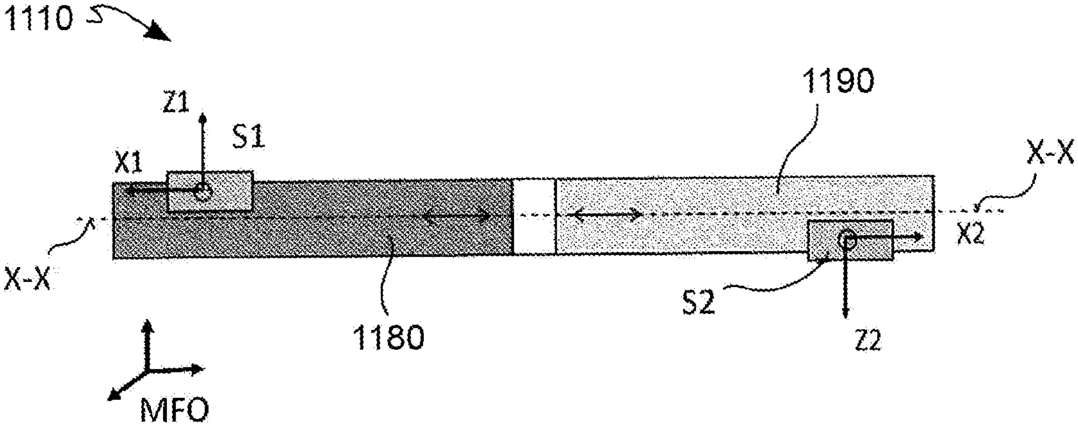
FIG. 11 shows an example of a master device to which an embodiment of the method and system of the invention refers.

FIG. 11 shows an embodiment in which the master device 1110 has a pen-like body, as previously mentioned, comprising two rigid parts 1180, 1190 constrained to translate co-linearly along a common axis X-X.

Figure 15:
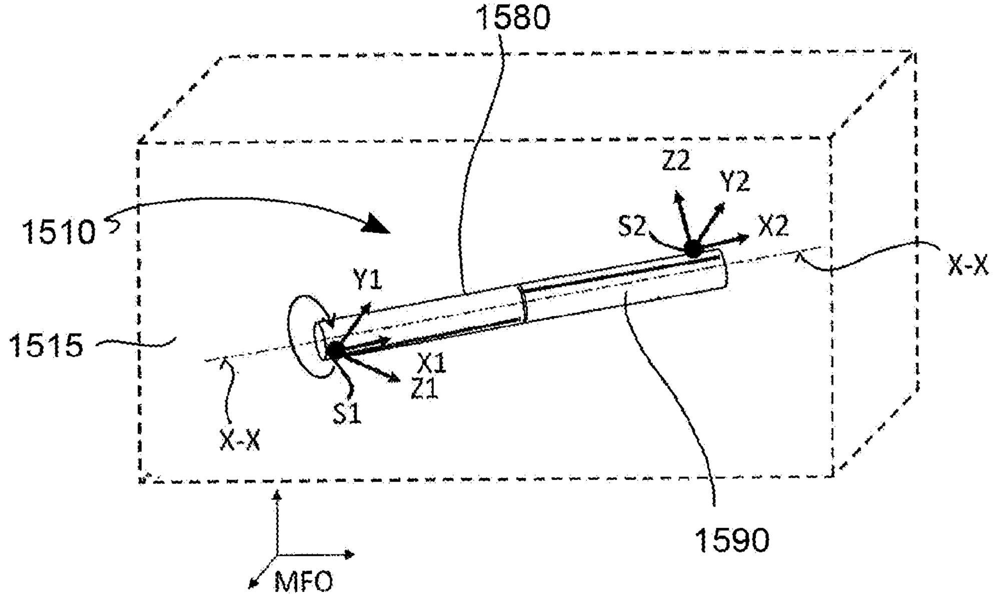
FIG. 15 diagrammatically shows an integrity verification example of a master device according to the embodiment in FIG. 11.

FIG. 15 shows an embodiment of an unconstrained master device 1510 within the workspace 1515 assigned thereto, in which the body of the master device 1510 is formed by two rigid parts 1580, 1590 constrained to translate co-linearly along a common axis X-X, in which verifying the integrity includes verifying the parallelism of the two sensors S1, S2 (in the shown example the rigid part 1580 is rotated about the longitudinal axis X1 thereof by an angle γ, and therefore the sensors S1 and S2 are not parallel to each other, which is indicative of an anomaly condition).

As can be seen, the objects of the present invention as previously indicated are fully achieved by the method described above by virtue of the features disclosed above in detail.

In fact, the method and system described allow an effective and real-time verification of the functional and structural integrity of the master device, and thus also allow detecting any anomalies in real time, and recognizing the type of anomaly.

As disclosed above, the principle shared by the above various embodiments is that the number of degrees of freedom measured is greater than the number of degrees of freedom allowed to the device.

For example, the measurements performed on the two parts of the master device provide 12 degrees of freedom (3 positions for the first portion of the master device, 3 positions for the second portion of the master device, 3 values representative of the rotation of the first master device coordinate frame associated with the first point, 3 values representative of the rotation of the second master device coordinate frame associated with the second point.

On the other hand, compared to the 12 degrees of freedom measured, the mechanical structure of the master device has only 7 degrees of freedom, which provides 5 degrees of freedom linked to mechanical constraints, and therefore, in principle, provides 5 different mathematical relations (which express such constraints) and which must be respected, so that it can be concluded that the master device is structurally intact.

The verification of such mathematical constraint relations, performed by the method in the different embodiments thereof, thus allows achieving the result of verifying the structural integrity of the master device.

Therefore, the method and system of the present disclosure meet the need to operate effective and reliable procedures for verifying the functional integrity of the master device, automatically and in real time.

Once a structural or functional anomaly of the master device has been identified, the teleoperation can be immediately and promptly interrupted, thus avoiding that such an anomaly is reflected in a consequent anomaly in the operation of the slave device and the surgical instrument associated therewith, intended to act on the patient, with possible consequences, even serious, on the patient himself.

Thereby, the objective of improving patient safety is achieved, meeting the very strict safety requirements which must be respected in the operating environment considered.

In order to meet contingent needs, those skilled in the art may make changes and adaptations to the embodiments of the method described above or can replace elements with others which are functionally equivalent, without departing from the scope of the following claims. All the features described above as belonging to a possible embodiment may be implemented irrespective of the other embodiments described.

The invention claimed is:

1. A method for verifying the structural and/or functional integrity of a master device, which is hand-held and unconstrained, used to control a robotic system for medical or surgical teleoperation, wherein the master device comprises a body comprising two rigid parts constrained to relatively rotate and/or translate with respect to a common axis, wherein the method comprises:

measuring and/or detecting position vectors of at least two points, each of which belonging to one respective rigid part of said two rigid parts of said master device, and measuring and/or detecting evolution over time of said at least two position vectors;

measuring and/or detecting an orientation of each of said at least two points, each orientation being expressed as a respective set of three numbers, and measuring and/or detecting the evolution over time of said orientations;

defining one or more constraints imposed by constructional or structural features of the master device, deriving from the difference between the number of degrees of freedom necessary to define a state of the master device and a number of information items detected, each constraint being associated with a mathematical relationship which must be respected in case of integrity of the master device;

calculating mathematical relations associated with each of the constraints defined, based on said detected and/or measured position vectors and orientations and on the respective evolutions over time;

determining a state of structural and/or functional integrity or non-integrity of the master device, based on a verification of whether or not the mathematical relations associated with each of the constraints defined are respected, utilizing the detected information related to the degrees of freedom that are redundant with respect to the information necessary to determine the state of the master device.

2. A method according to claim 1, wherein the robotic system for medical or surgical teleoperation comprises:

said master device, mechanically ungrounded and adapted to be hand-held by a surgeon during surgery, and configured to detect a manual command of the surgeon and generate a respective first electrical command signal;

at least one slave device, or slave robotic assembly, comprising at least one slave surgical instrument configured to operate on a patient, in a manner controlled by the master device;

a control unit provided with a computer, configured to receive said first electrical command signal from the master device, generate a second electrical command signal, based on the first electrical command signal, and provide the second electrical command signal to the slave robotic assembly, to actuate the at least one slave surgical instrument;

wherein said control unit is operatively connected to one or more sensors configured to perform said detecting and/or measuring steps;

and wherein the control unit is configured to receive and process third electrical control signals representative of said detected and/or measured position vectors and of the related evolution over time, and wherein said calculating and determining steps are performed by said control unit, in which said one or more constraints and the respective mathematical relations are stored.

3. A method according to claim 1, wherein said measuring and/or detecting steps comprise:

measuring and/or detecting said position vectors and orientations, and the related evolutions over time, with respect to a first reference frame associated with the robotic system for surgical or medical teleoperation, and having predetermined axes and origin at a preset point.

4. A method according to claim 3, wherein the robotic system for surgical or medical teleoperation further comprises at least one tracking system for detecting input position and orientation of the master device within a predetermined tracking volume, so that actuation of a slave surgical instrument depends on a manual command given by a surgeon by the master device and/or on the position and orientation of the master device.

5. A method according to claim 3, wherein said measuring and/or detecting steps are performed by two or more magnetic sensors, each of the magnetic sensors being arranged at a respective one of said at least two points belonging to the master device, and being configured to detect respective local values of a magnetic field generated by a magnetic field generator constrained to a part of the robotic system for surgical or medical teleoperation, and wherein said first reference frame has an origin at said magnetic field generator, and comprises three orthogonal axes, and wherein, said magnetic field generator belongs to at least one tracking system, and/or wherein said measuring and/or detecting steps are performed by at least one optical sensor or camera, associated with and/or constrained to said robotic system for teleoperated surgery, and wherein said first reference frame is an internal reference frame of the optical sensor or camera, and wherein said optical sensor or camera belongs to said at least one tracking system.

6. A method according to claim 3, wherein the method further comprises:

defining a second reference frame and a third reference frame associated with said at least two points of the master device, respectively, wherein each of said second reference frame and third reference frame comprises:

a respective origin, corresponding to the respective point;

a respective first axis aligned with the respective rigid part of the master device with which the respective point is associated;

a respective second axis parallel to the rotation axis of the two rigid parts of the master device, or perpendicular to translation axis of one rigid part of the master device with respect to the other rigid part;

a respective third axis orthogonal to both the first axis and the second axis so as to form a levorotatory set of three axes;

and wherein:

said step of measuring and/or detecting the position vectors and the related evolution over time comprises measuring and/or detecting the position of the origin, and the related evolution over time, of the second reference frame and third reference frame with respect to the first reference frame;

said step of measuring and/or detecting the orientation and the related evolution over time comprises measuring and/or detecting the orientation, and the related evolution over time, of the second reference frame and third reference frame with respect to the first reference frame.

7. A method according to claim 1, wherein said at least two points belonging to the master device comprise:

a tip or free end of a first rigid part or rigid bar or rigid arm of the master device;

a tip or free end of a second rigid part or rigid bar or rigid arm of the master device, wherein said rigid parts or bars or arms are articulated to each other or otherwise constrained to rotate or translate about a common axis.

8. A method according to claim 1, wherein a command given by a surgeon corresponds to a variation of the opening angle between said two rigid parts, and wherein the method comprises the further step of calculating a positional set of three numbers and a rotational set of three numbers of a reference point and an opening angle of the master device, based on the detected vectors, wherein said reference point comprises one of the following points:

midpoint between the two tips; and/or center of gravity of the master device; and/or master device joint; or wherein the two rigid parts translate with respect to each other in a direction coinciding with a longitudinal extension of the master device body, said two rigid parts being integral with each other in rotations about the longitudinal extension of the master device body, and wherein the command given by the surgeon corresponds to a translation of one rigid part with respect to the other; and wherein the method comprises the further step of calculating the positional set of three numbers and the rotational set of three numbers of a first sensor associated with a first reference point on the first rigid part, and of a second sensor associated with a second reference point on the second rigid part, based on the detected vectors.

9. A method according to claim 1, wherein the step of determining a state of integrity comprises:

confirming the state of integrity if all the defined constraints are respected, within predetermined tolerance limits;

identifying the state of non-integrity if at least one of the defined constraints is not respected, even after taking into account predetermined tolerance limits.

10. A method according to claim 1, wherein said constraint comprises:

the detected points corresponding to said at least two points, wherein the position vectors of the detected points are measured or detected, and wherein the detected points must lie on a same plane, within a coplanarity tolerance limit.

11. A method according to claim 1, wherein the master device comprises a rotational joint, and wherein said constraint comprises:

the detected points corresponding to said at least two points wherein the position vectors of the detected points are measured or detected, and wherein the detected points must project always in a same predetermined manner on an orthogonal plane defined by normal axes parallel to the joint axis, passing through said two points, a vector product between the two vectors joining the rotational joint and the two points, respectively, must always be concordant or discordant with the vector associated with one of said normal axes, wherein a concordance or discordance condition is predetermined based on constructional features of the master device.

12. A method according to claim 1, wherein the master device comprises a prismatic joint, and wherein said constraint comprises:

the detected points corresponding to said at least two points, wherein the position vectors of the detected points are measured or detected, and wherein the detected points must project always in the same predetermined manner onto an orthogonal plane defined by the axes, coplanar to the master device and perpendicular to a direction defined by the two rigid parts.

13. A method according to claim 1, wherein said constraint comprises:

normal axes parallel to a joint axis, passing through said at least two points, wherein the position vectors of the detected points are measured or detected, and wherein the detected points must be parallel and concordant, within a parallelism acceptability limit.

14. A method according to claim 1, wherein said constraint comprises:

considering pairs consisting of each of the two points and the respective axis joining the point to a joint, and translating each point along the corresponding axis by a linear metric quantity, two respective translated points are obtained, which must have a distance less than a maximum allowed distance between translated points.

15. A method according to claim 1, wherein said constraint comprises:

a distance between said at least two points, wherein the position vectors of said at least two points are measured or detected, and wherein the distance cannot exceed a distance at which said at least two points are under maximum opening conditions of the master device, and, where applicable, the distance cannot be less than a minimum distance measured at a minimum opening of the master device, wherein said maximum opening of the master device and said minimum opening of the master device are predetermined parameters, depending on constructional features of the master device.

16. A method according to claim 1, wherein all quantities of said constraint are either detected, or calculated, in real time, by virtue of measurements performed which provide 12 degrees of freedom, 5 of the degrees of freedom being redundant, and wherein whether said constraints are respected or not is verified in real time;

if at least one of the constraints is not respected, an anomaly is detected in real time.

17. A method according to claim 1, further comprising the steps of calculating, based on the quantities detected, the following parameters:

planarity between axes, measured in degrees;

maximum distance between sensors;

distance between an origin of a reference frame of a sensor and a plane of an other sensor;

distance between two lines of master device arms, and wherein said constraints to be verified are:

said at least two points belong to the same plane, wherein the position vectors of said at least two points are measured or detected;

normal axes must be parallel;

further points which are obtained by moving said at least two points, respectively, backwards on the arms by a known length must both coincide with a point which corresponds to a joint and origin of a Master Frame Joint reference frame;

an opening angle of the master device must be lower than a maximum value;

a maximum distance between said at least two points must be lower than a maximum value.

18. A method according to claim 1, wherein the step of verifying the functional integrity of the master device further comprises the step of detecting/quantifying noise associated with detection of an instantaneous position vector to understand if there is perturbation by an external magnetic field, and/or defining an instantaneous acceptability threshold.

19. A method for managing anomalies of a master device comprising carrying out the method for verifying the structural integrity, according to claim 1, wherein any non-compliance with the constraint involves immediate interruption of the teleoperation and of movements of a surgical instrument associated with a slave device, and/or wherein the method further comprising the steps of:

providing information about an outcome of verification to a control system of the robotic system; and/or communicating information obtained to a robotic system state machine, and/or a user interface and/or an endpoint on a slave side.

20. A robotic system for medical or surgical teleoperation comprising:

a master device, mechanically ungrounded and configured to be hand-held by a surgeon during surgery, and to detect a manual command of a surgeon and generate a respective first electrical command signal, said master device comprising a body comprising two rigid parts constrained to relatively rotate and/or translate with respect to a common axis;

at least one slave device, or slave robotic assembly, comprising at least one slave surgical instrument configured to operate on a patient, in a manner controlled by the master device;

a control unit provided with a computer, configured to receive said first electrical command signal from the master device, generate a second electrical command signal, based on the first electrical command signal, and provide the second electrical command signal to the slave robotic assembly, to actuate the at least one slave surgical instrument;

wherein the system is configured to perform the following actions:

measuring and/or detecting position vectors of at least two points, each of the at least two points belonging to one respective of said two rigid parts of said master device, and measuring and/or detecting evolution over time of said at least two position vectors;

measuring and/or detecting an orientation of each of said at least two points, each orientation being expressed as a respective set of three numbers, and measuring and/or detecting evolution over time of said orientations;

defining one or more constraints, or storing one or more predetermined constraints, said constraints being imposed by constructional or structural features of the master device, deriving from a difference between a number of degrees of freedom necessary to define a state of the master device and a number of information items detected, each constraint being associated with a mathematical relation which must be respected in a case of integrity of the master device;

calculating mathematical relations associated with each of the constraints defined, based on said detected and/or measured position vectors and orientations and on the respective evolutions over time;

determining a state of structural and/or functional integrity or non-integrity of the master device, based on a verification of whether or not the mathematical relations associated with each of the constraints defined are respected, utilizing the detected information related to the degrees of freedom that are redundant with respect to the information necessary to determine the state of the master device.

* * * * *